(12) United States Patent
Dahler et al.

(10) Patent No.: US 8,408,082 B2
(45) Date of Patent: Apr. 2, 2013

(54) APPARATUS TO MEASURE FLUIDS IN A CONDUIT

(75) Inventors: Steven E. Dahler, Ballston Spa, NY (US); Peter Alan Gregg, Niskayuna, NY (US); Christopher R. Banares, Ballston Spa, NY (US)

(73) Assignee: General Electric Company, Schenectady, NY (US)

( * ) Notice: Subject to any disclaimer, the term of this patent is extended or adjusted under 35 U.S.C. 154(b) by 499 days.

(21) Appl. No.: 12/620,949

(22) Filed: Nov. 18, 2009

(65) Prior Publication Data

US 2011/0113899 A1  May 19, 2011

(51) Int. Cl.
  *G05D 3/12* (2006.01)
  *G01D 11/00* (2006.01)
  *G01N 1/02* (2006.01)
  *G01N 1/22* (2006.01)
  *F16H 57/00* (2012.01)

(52) U.S. Cl. ........... 73/866.5; 73/863.01; 73/863.82; 74/84 R; 74/89; 74/110; 74/113

(58) Field of Classification Search ........... 73/23.31, 73/863.01, 863.82, 865.8, 866.5; 74/18, 74/18.2, 25, 29, 84 R, 88–89, 110, 113, 120, 74/128, 130; 173/11; 254/93 R, 95, 97; 414/749.1, 749.3; 483/7, 11; 700/228, 275, 700/302

See application file for complete search history.

(56) References Cited

U.S. PATENT DOCUMENTS

| | | | |
|---|---|---|---|
| 3,199,373 A * | 8/1965 | Veale | 74/84 R X |
| 3,200,656 A * | 8/1965 | Baskett | 74/110 X |
| 3,524,784 A * | 8/1970 | Isaksson et al. | 156/367 |
| 3,984,745 A * | 10/1976 | Minalga | 318/567 |
| 4,016,768 A | 4/1977 | Mashburn et al. | |
| 4,169,758 A * | 10/1979 | Blackstone et al. | 376/249 |
| 4,428,055 A * | 1/1984 | Zurbrick et al. | 700/160 |
| 4,562,392 A * | 12/1985 | Davis et al. | 318/572 |
| 4,606,587 A | 8/1986 | Thompson | |
| 4,621,431 A | 11/1986 | Fatool et al. | |
| 4,667,550 A * | 5/1987 | Eiting | 83/56 |
| 5,394,759 A | 3/1995 | Taina | |
| 5,440,217 A | 8/1995 | Traina | |
| 5,507,192 A | 4/1996 | Beaudin | |

(Continued)

FOREIGN PATENT DOCUMENTS

EP  529796 A1 * 3/1993
EP  0620419 A1  10/1994

(Continued)

OTHER PUBLICATIONS

GB Search Report issued in connection with corresponding GB Patent Application No. 1018751.6 filed on Nov. 8, 2010.

*Primary Examiner* — Thomas P Noland
(74) *Attorney, Agent, or Firm* — Armstrong Teasdale LLP

(57) ABSTRACT

A transport device includes a first segment fixedly coupled to a wall. The transport device also includes at least one second segment coupled to the first segment. The at least one second segment includes at least one of a fluid-driven device, a rack and pinion drive device, and a carriage. The transport device further includes an automated position control system. The control system includes at least one axial positioning device coupled to the at least one second segment. The control system also includes at least one axial position feedback device coupled to at least one of the first segment and the at least one second segment.

11 Claims, 19 Drawing Sheets

U.S. PATENT DOCUMENTS

| | | |
|---|---|---|
| 5,509,313 A | 4/1996 | Traina et al. |
| 5,520,048 A | 5/1996 | Traina et al. |
| 5,635,652 A | 6/1997 | Beaudin |
| 6,083,082 A * | 7/2000 | Saldana ............................ 451/5 |
| 6,094,993 A | 8/2000 | Traina |
| 6,233,497 B1 * | 5/2001 | Kachi et al. ................... 700/173 |
| 6,539,642 B1 | 4/2003 | Moriyasu et al. |
| 7,065,893 B2 | 6/2006 | Kassai et al. |
| 7,472,615 B2 | 1/2009 | Mayeaux |
| 7,520,067 B2 | 4/2009 | Yoshizumi et al. |
| 2006/0156836 A1 * | 7/2006 | Ny et al. ...................... 73/866.5 |
| 2007/0219561 A1 * | 9/2007 | Lavallee et al. ................. 606/90 |
| 2007/0227273 A1 * | 10/2007 | Layton et al. ................ 73/865.8 |

FOREIGN PATENT DOCUMENTS

| | | |
|---|---|---|
| EP | 663715 A2 * | 7/1995 |
| EP | 1930289 A2 * | 6/2008 |
| GB | 2181219 A | 4/1987 |
| JP | 62277536 A | 12/1987 |
| WO | 02/26341 A2 | 4/2002 |
| WO | WO 03050783 A1 * | 6/2003 |

* cited by examiner

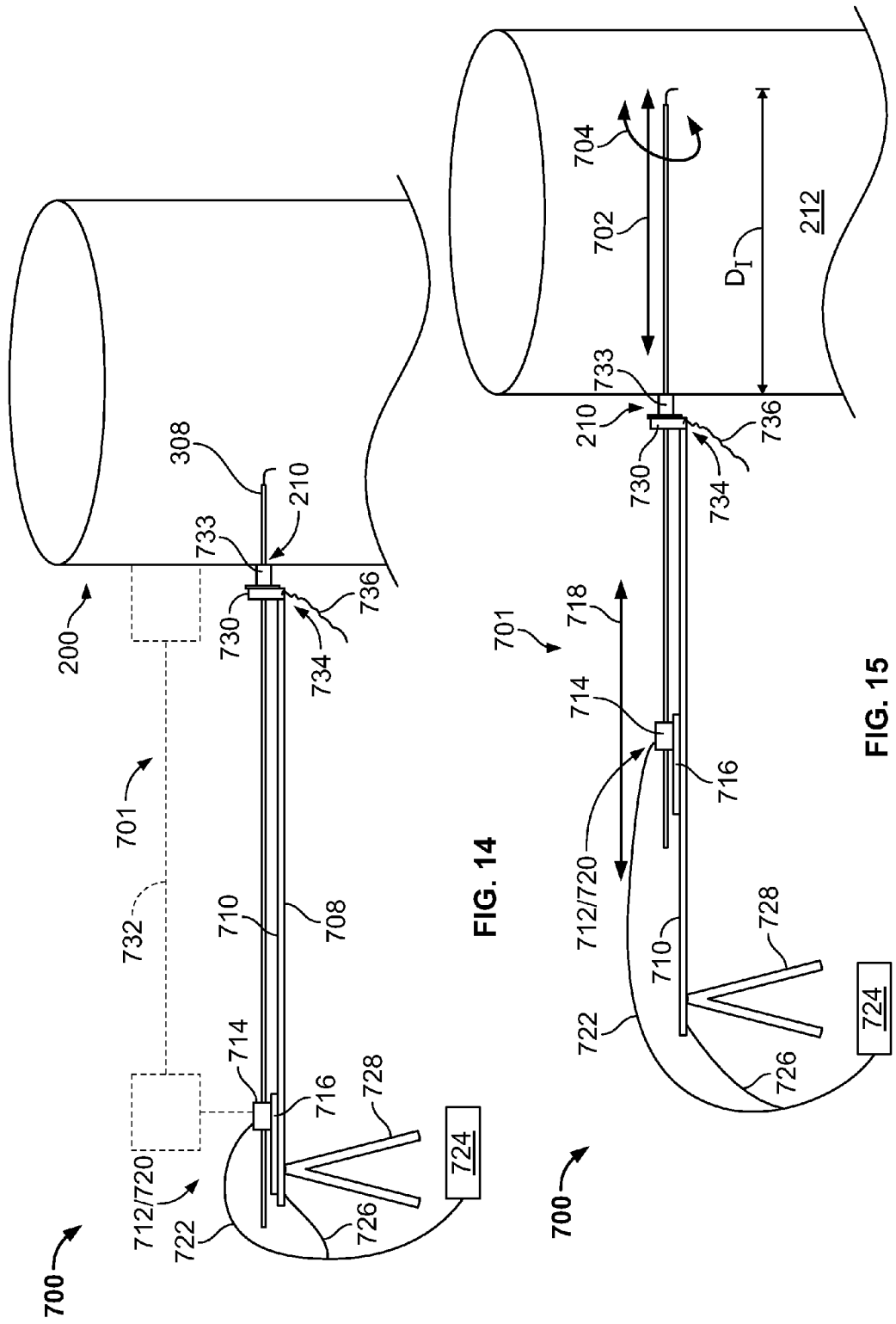

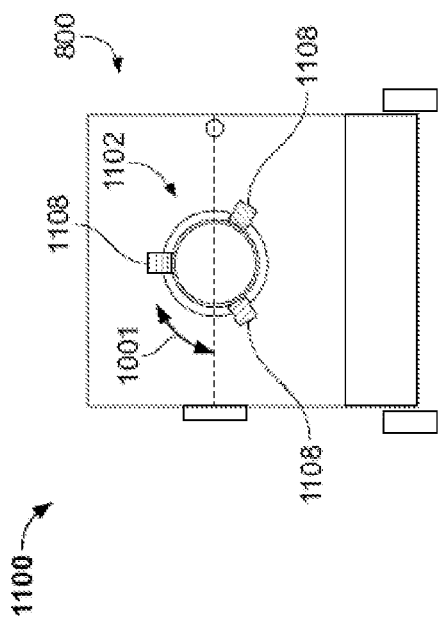
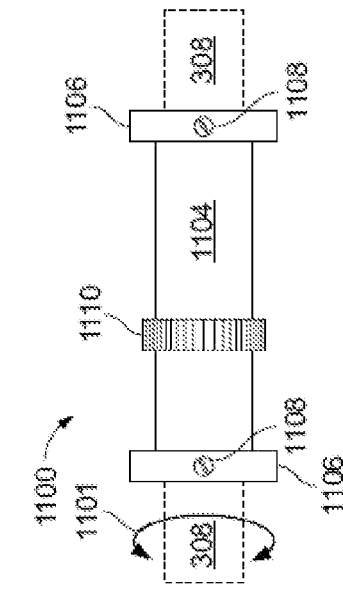
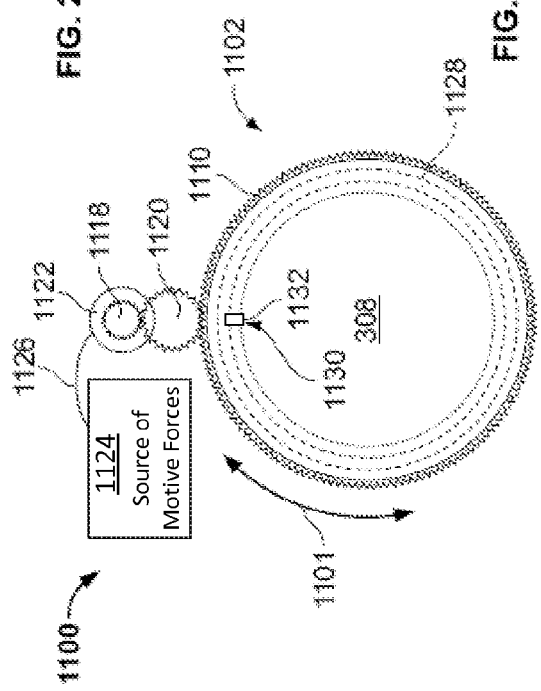
FIG. 20
FIG. 21
FIG. 22

APPARATUS TO MEASURE FLUIDS IN A CONDUIT

BACKGROUND OF THE INVENTION

The embodiments described herein relate generally to fluid measurement and fluid sampling devices, and more particularly, to apparatus for use in measuring emissions in exhaust stacks.

At least some known production facilities include equipment and processes that may generate monitored and regulated emissions constituents, for example, nitrogen oxides ($NO_x$) and carbon monoxide (CO). At least some known production facilities include electric power generation plants, food processing plants, and waste elimination plants. For example, in some known electric power generation plants, fossil fuels are combusted, thereby generating hot combustion gases that are channeled to a turbo-generator. At least some of the thermal energy contained in the hot combustion gases is converted to rotational energy within the turbo-generator. An exhaust fluid stream that includes the thermally-expended combustion gases that include the monitored and regulated constituents is channeled from the turbo-generator to an exhaust stack prior to being exhausted to atmosphere. Such an exhaust fluid stream may include emissions that are monitored.

Emissions monitoring apparatus is typically used to sample the exhaust fluid and measure the regulated constituents channeled therein. Such apparatus may include permanently installed equipment proximate to an exhaust stack or duct for long-term monitoring and/or may include temporarily installed equipment proximate to the exhaust stack or duct for short-term testing. At least some known emissions monitoring and testing apparatus includes a probe that is extended into the exhaust fluid stream to measure exhaust emissions parameters, such as stream velocity profiles and constituent concentrations within the stream. These known monitoring and testing apparatus extract samples of the exhaust fluid stream. Testing and monitoring activities often include sampling at multiple points along a cross-section of the stack or duct. Therefore, some known emissions monitoring apparatus include extendible devices that penetrate the stack or duct via extension and retraction as needed. Many known extendible devices have length dimensions that enable measurements of the exhaust fluid stream, however, such probes have a large physical footprint in the vicinity of the stack or duct. Moreover, some known emissions monitoring apparatus include fixed and/or non-extendible devices that require manual extension, retraction, and other positioning as needed. Emissions testing typically requires reduced production during such testing activities. Therefore, using manual emissions measuring and sampling apparatus extends a period of time required for sampling and testing activities at lower production levels, thereby reducing revenue-based production and/or increasing production costs.

BRIEF DESCRIPTION OF THE INVENTION

This Brief Description is provided to introduce a selection of concepts in a simplified form that are further described below in the Detailed Description. This Brief Description is not intended to identify key features or essential features of the claimed subject matter, nor is it intended to be used as an aid in determining the scope of the claimed subject matter.

In one aspect, a transport device includes a first segment fixedly coupled to a wall. The transport device also includes at least one second segment coupled to the first segment. The at least one second segment includes at least one of a fluid-driven device, a rack and pinion drive device, and a carriage. The transport device further includes an automated position control system. The control system includes at least one axial positioning device coupled to the at least one second segment. The control system also includes at least one axial position feedback device coupled to at least one of the first segment and the at least one second segment.

In another aspect, a fluid sampling system is provided. The Fluid sampling system includes at least one fluid sampling device that partially extends through at least one fluid measuring probe port defined in at least a portion of a conduit. The at least one fluid sampling device includes at least one probe segment that is rotatably coupled to at least one probe rotary positioning mechanism. The at least one probe segment includes at least one of a motor-driven gear-drive device and a fluid-driven device. The at least one probe rotary positioning mechanism also includes an automated position control system coupled to the at least one probe rotary positioning mechanism and including at least one position feedback device.

In yet another aspect, another fluid sampling system is provided. The fluid sampling system includes at least one fluid sampling device that partially extends through at least one fluid measuring probe port defined in at least a portion of a conduit. The at least one fluid sampling device includes a fixed segment coupled to at least a portion of the conduit. The device also includes at least one telescoping segment coupled to the fixed segment. The device further includes at least one probe segment rotatably coupled to the at least one telescoping segment. The device also includes an automated position control system including at least one of at least one axial positioning device coupled to the at least one telescoping segment, at least one axial position feedback device coupled to at least one of the fixed segment and the at least one telescoping segment, at least one probe rotary positioning mechanism coupled to the at least one probe segment, and at least one rotary position feedback device.

BRIEF DESCRIPTION OF THE DRAWINGS

FIG. 14 is a schematic cross-sectional view of an alternative sampling probe transport device in a retracted position that may be used with the exhaust stack shown in FIG. 2;

FIG. 15 is a schematic cross-sectional view of the sampling probe transport device shown in FIG. 14 in an extended position;

FIG. 20 is a schematic axial view of an alternative rotational positioning device that may be used with the sampling probe transport devices shown in FIGS. 14, 15, 17, and 18;

FIG. 21 is a schematic cross-sectional view of the rotational positioning device shown in FIG. 20;

FIG. 22 is another schematic axial view of the rotational positioning device shown in FIGS. 20 and 21;

DETAILED DESCRIPTION OF THE INVENTION

Figure 1:
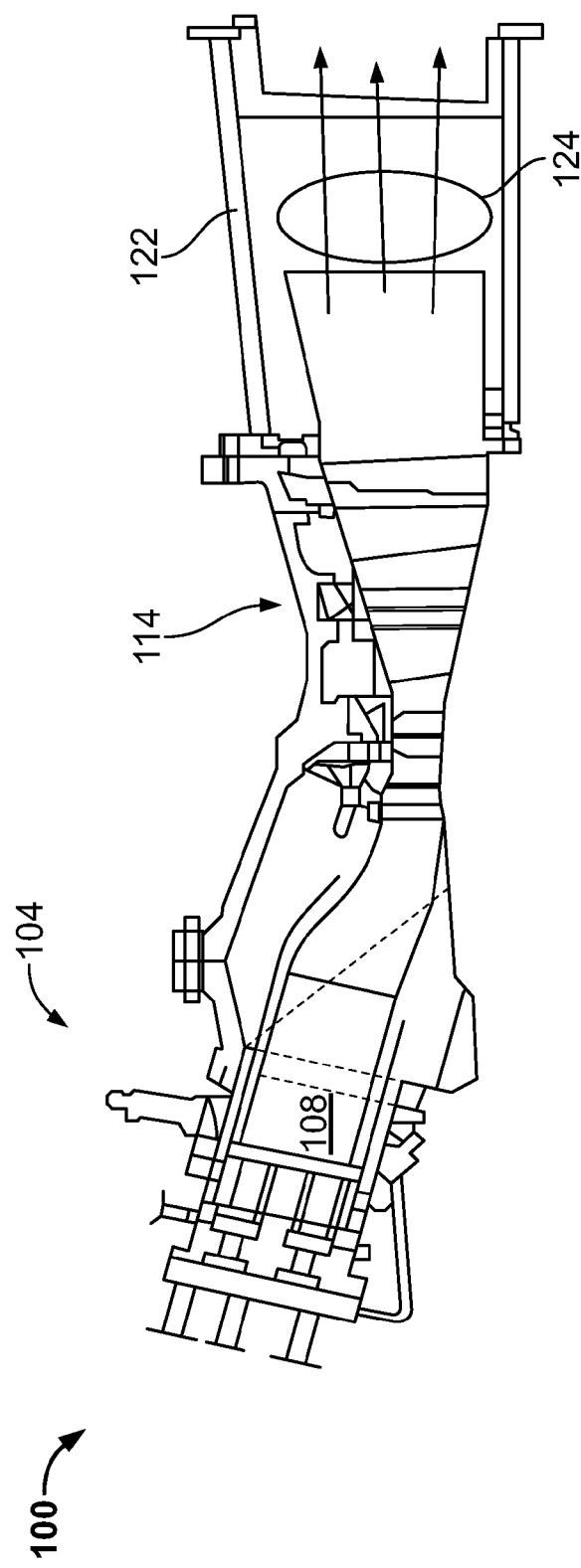
FIG. 1 is a schematic cross-sectional view of an exemplary turbine engine.

FIG. 1 is a schematic cross-sectional view of an exemplary exhaust-producing facility 100. Specifically, in the exemplary embodiment, facility 100 is an exemplary gas turbine engine. Alternatively, exhaust-producing facility 100 maybe any facility that produces an exhaust fluid with monitored emissions, such as, but not limited to, chemical production plants, food processing plants, coal-fired power plants, and trash incineration facilities. In the exemplary embodiment, engine 100 includes a plurality of combustor assemblies 104 (only one shown in FIG. 1) that at least partially defines a combustion chamber 108. Engine 100 also includes a turbine assembly 114 that is coupled in flow communication with combustion chamber 108. An exhaust duct 122 is coupled in flow communication with turbine assembly 114.

In operation, compressed air and fuel are channeled to combustion chamber 108. In the exemplary embodiment, combustor assembly 104 ignites and combusts fuel, for example, synthetic gas (syngas) within combustion chamber 108 and generates a high temperature combustion gas stream (not shown) of approximately 1316 degrees Celsius (° C.) to 1593° C. (2400 degrees Fahrenheit (° F.) to 2900° F.). Alternatively, assembly 104 combusts fuels that include, but are not limited to, natural gas and/or fuel oil. The combustion gas stream is channeled to turbine 114 and gas stream thermal energy is converted to mechanical rotational energy and the temperature of the gas stream is decreased and forms an exhaust fluid stream 124 that may have a temperature of approximately 93° C. (200° F.) to approximately 649° C. (1200° F.). Exhaust stream 124 is channeled from turbine assembly 114 to exhaust duct 122.

Figure 2:
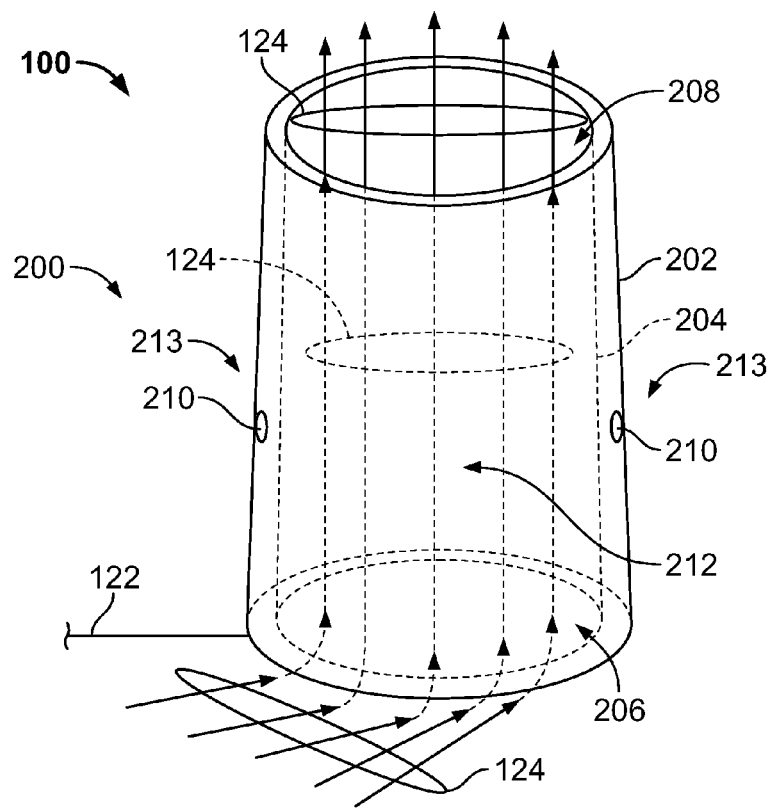
FIG. 2 is a schematic perspective view of an exemplary exhaust stack that may be used with the turbine engine shown in FIG. 1.

FIG. 2 is a schematic perspective view of an exemplary exhaust stack 200 that may be used with gas turbine engine 100, for example. In the exemplary embodiment, exhaust duct 122 is coupled in flow communication with exhaust stack 200. Stack 200 includes an outer wall 202 coupled to an inner liner 204, that are oriented such that wall 202 and liner 204 define an exhaust fluid entry port 206. An atmospheric exhaust port 208, at least one exhaust fluid measuring probe port 210, and an exhaust conduit 212 are between ports 206 and 208. In the exemplary embodiment, an exhaust stack fluid measuring system 213 includes an exhaust fluid measuring probe (not shown in FIG. 2) that is inserted within each measuring probe port 210. Exhaust fluid monitoring, measuring, and sampling can be performed within duct 122 in conjunction with, or in lieu of, stack 200.

In operation, exhaust fluid stream 124 discharged from exhaust duct 122 into exhaust stack 200 via entry port 206. Exhaust stack 200 channels exhaust fluid stream 122 from entry port 206 to exhaust port 208 via conduit 212 and stream 124 is exhausted to atmosphere. Measuring probes (not shown in FIG. 2) are inserted into stream 124 within stack 200 via ports 210.

Figure 3:
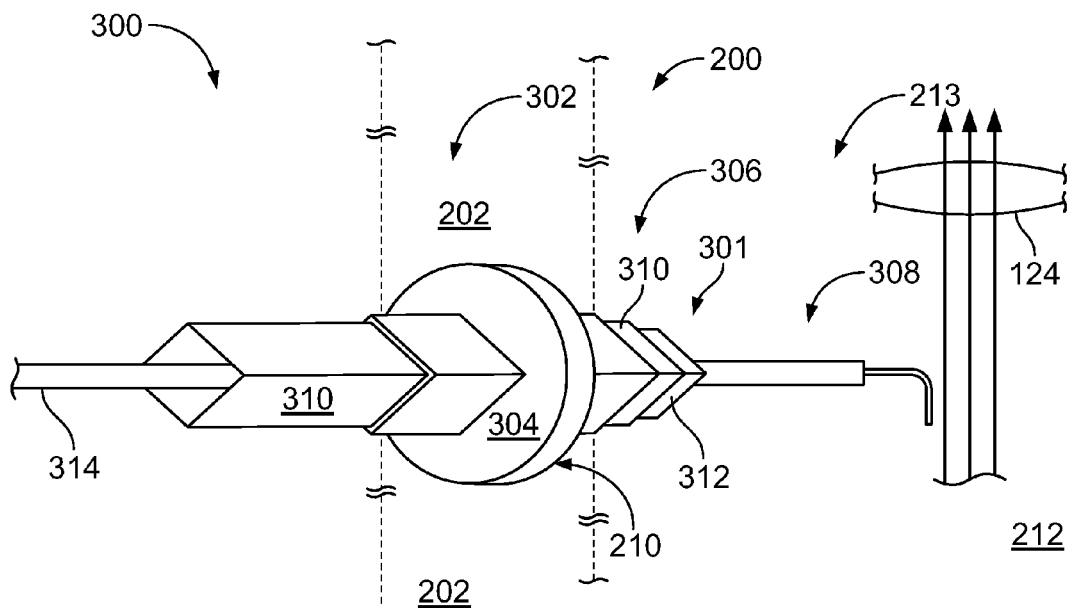
FIG. 3 is a schematic perspective view of an exemplary sampling probe transport device, in a retracted position, that may be used with the exhaust stack shown in FIG. 2.
Figure 4:
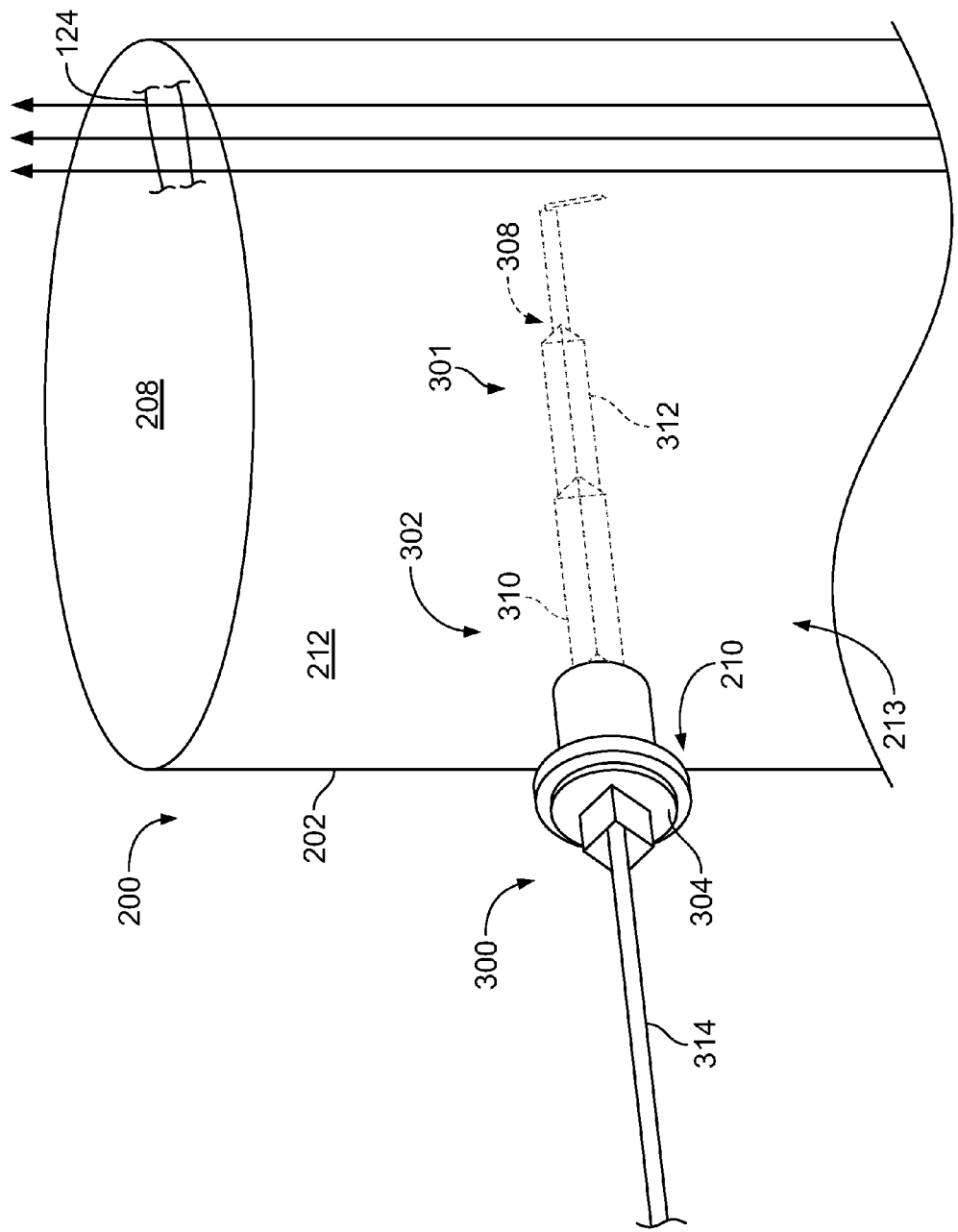
FIG. 4 is a schematic perspective view of the sampling probe transport device shown in FIG. 3 in an extended position.

FIG. 3 is a schematic perspective view of an exemplary sampling probe transport device 300 in a retracted position that may be used with exhaust stack 200 and exhaust stack fluid measuring system 213. FIG. 4 is a schematic perspective view of sampling probe transport device 300 in an extended position. As used herein, sampling and measuring are used interchangeably. In the exemplary embodiment, device 300 includes a plurality of segments 302 that include a first or fixed segment 304, a plurality of second or concentrically-aligned telescoping segments or tubes 306, and at least one probe segment 308. In the exemplary embodiment, device 300 and probe segment 308 are assembled to form a fluid sampling device 301. Device 300 transports, or more specifically, extends and retracts probe segment 308 within exhaust stack 200 as discussed further below.

As used herein, telescoping is defined as the characteristic of a plurality of concentrically-aligned tubes slidingly moving with respect to each other thereby either lengthening/extending and/or shortening/retracting an object. Specifically, in the exemplary embodiment, an axial extension and retraction assembly, or more specifically, telescoping tubes 306 include two segments or tubes, that is, an outer telescoping segment or tube 310, and an inner telescoping segment or tube 312. Alternatively, tubes 306 may include any number of tubes 306 that enable operation of device 300 as described herein.

Also, in the exemplary embodiment, tubes 310 and 312 have a substantially square and/or rhomboid cross-sectional shape. More specifically, in the exemplary embodiment, tubes 310 and 312 have a diamond-shaped cross-sectional shape. The cross-sectional shape of tubes 310 and 312 facilitates alignment between segment 304 and tubes 310 and 312. Alternatively, tubes 310 and 312 may have any cross-sectional shape that enables operation of device 300 as described herein, including, but not limited to cylindrically-shaped, ovally-shaped, and triangularly-shaped cross-sections. Further, in the alternative embodiment, device 300 includes at least one device services conduit 314. Conduit 314 houses services apparatus that include, but are not limited to, sample conduits, cooling conduits, and signal and electrical power transmission conduits (neither shown in FIGS. 3 and 4). Moreover, conduit 314 is any type of conduit that enables operation of device 300 as described herein such as, but not limited to, electrical conduit, piping, and helical cords. As described herein, sampling probe transport device 300 facilitates reducing a physical footprint of each of devices 300 in the vicinity of exhaust stack 200. Reducing such a physical footprint facilitates increasing personal access and increasing available space for other equipment in the vicinity of exhaust stack 200. Moreover, reducing a size of device 300 reduces material and manufacturing costs and shipping costs.

Figure 5:
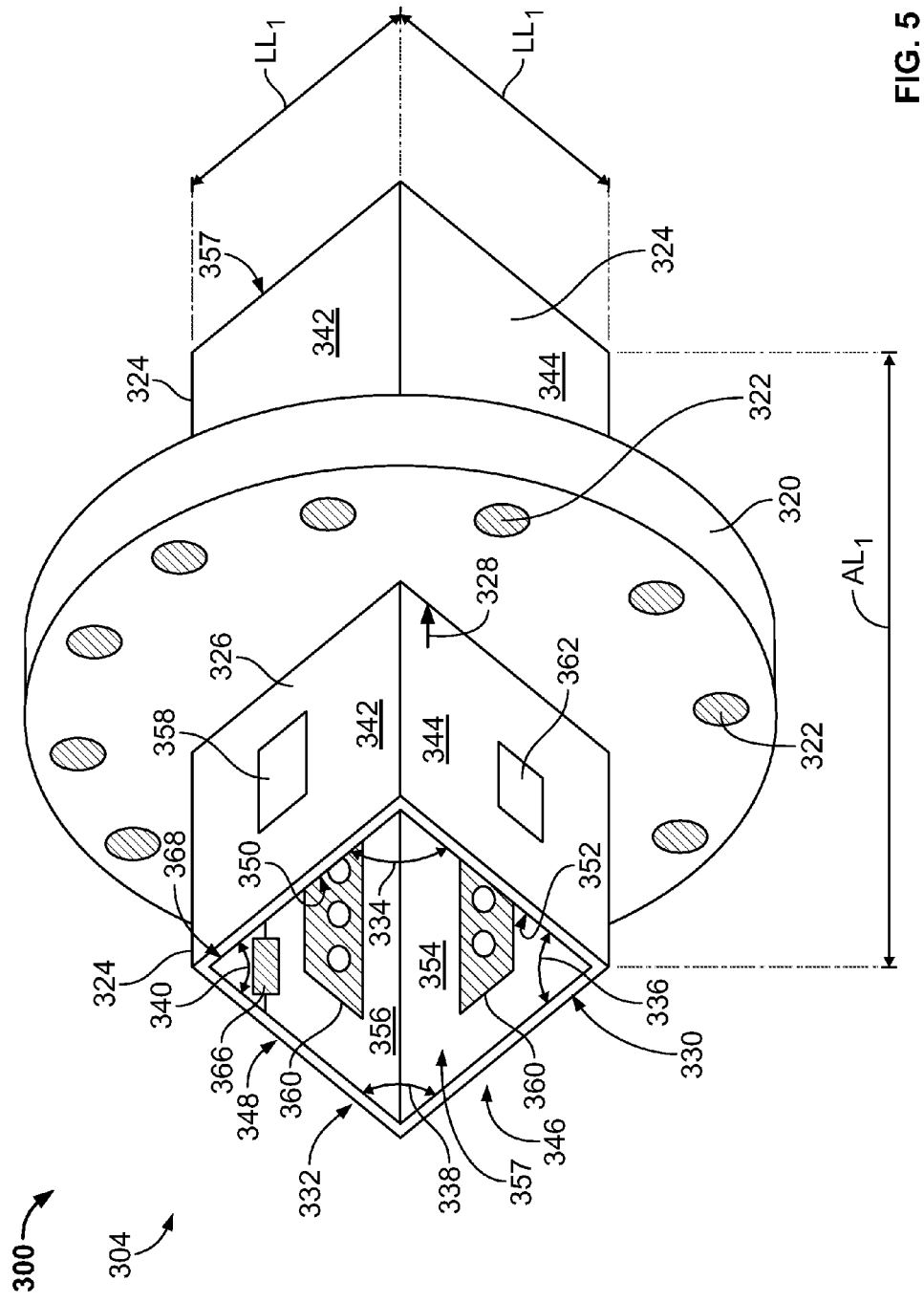
FIG. 5 is a schematic perspective view of an exemplary fixed segment that may be used with the sampling probe transport device shown in FIGS. 3 and 4.
Figure 6:
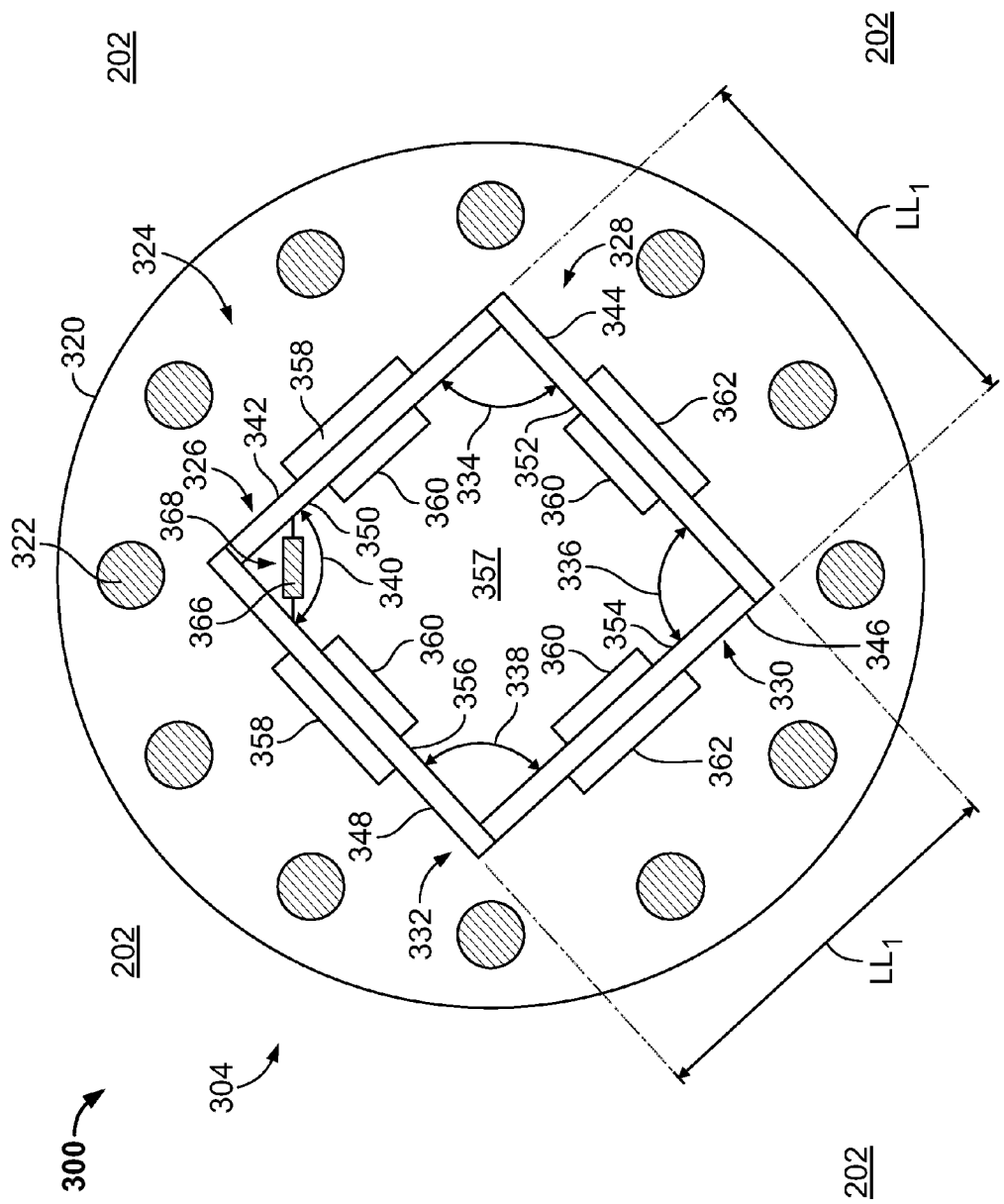
FIG. 6 is a schematic axial view of the fixed segment shown in FIG. 5, and external to the exhaust stack shown in FIG. 2.
Figure 7:
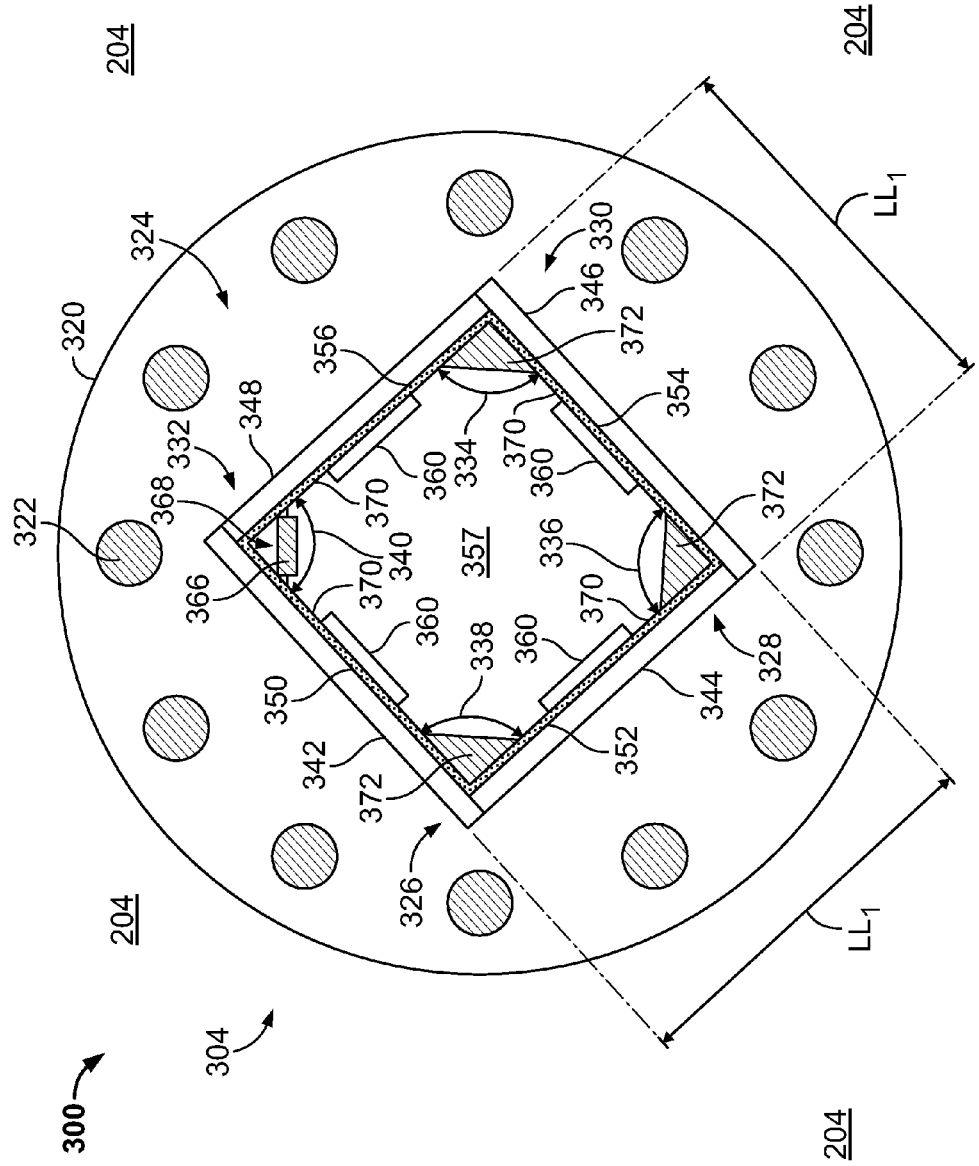
FIG. 7 is a schematic axial view of the fixed segment that is shown in FIG. 5, and internal to the exhaust stack shown in FIG. 2.

FIG. 5 is a schematic perspective view of exemplary fixed segment 304 that may be used with sampling probe transport device 300. FIG. 6 is a schematic axial view of fixed segment 304 external to exhaust stack 200 (shown in FIGS. 2, 3, and 4). FIG. 7 is a schematic axial view of fixed segment 304 internal to exhaust stack 200. In the exemplary embodiment, fixed segment 304 includes a flange portion 320 that defines a plurality of fastener openings 322. Segment 304 extends through, and is coupled to, stack outer wall 202 via fasteners (not shown) that include, but are not limited to, only including bolts. Alternatively, segment 304 is coupled to wall 202 via any fastening method that enables operation of device 300 as described herein.

Also, in the exemplary embodiment, fixed segment 304 includes a support duct 324 that is coupled to flange portion 320. Further, in the exemplary embodiment, support duct 324 includes four substantially identical sides 326, 328, 330, and 332. Support duct 324 is substantially square and sides 326, 328, 330, and 332 have substantially similar dimensions that facilitate receiving outer telescoping tube 310. Specifically, each side 326, 328, 330, and 332 defines a longitudinal length of $LL_1$. Moreover each side 326, 328, 330, and 332 defines an axial length $AL_1$ that is substantially bifurcated by flange portion 320 to facilitate providing cantilevered support of device 300 when it is fully extended. Therefore, in the exemplary embodiment, sides 326, 328, 330, and 332 define four substantially equal dihedral angles 334, 336, 338, and 340 of approximately 90° each. Alternatively, support duct 324 has a rhomboid cross-sectional shape and angles 334, 336, 338, and 340, and dimensions $LL_1$ and $AL_1$ have any values that enable operation of device 300 as described herein.

Further, in the exemplary embodiment, each side 326, 328, 330, and 332 defines an outer surface 342, 344, 346, and 348, respectively, and an inner surface 350, 352, 354, and 356, respectively. Surfaces 350, 352, 354, and 356 define a cavity 357 that is sized to receive outer telescoping tube 310 (shown in FIGS. 3 and 4) therein. A mounting pad 358 for a push chain winch (not shown in FIGS. 5, 6 and 7) is coupled to outer surfaces 342 and 348. Also, a ball bearing strip 360 is coupled to each inner surface 350, 352, 354, and 356, such that each strip 360 is slidingly coupled to an opposing outer surface (not shown in FIGS. 5, 6, and 7), as described in more detail below. Alternatively, sliding engagement of surfaces 350, 352, 354, and 356 with opposing outer surfaces of tube 310 is accomplished via any other method that enables operation of device 300 as described herein including, but not limited to, ball bearing configurations and/or friction-resistant tapes and coatings. Further, a mounting pad 362 for a rotary drive mechanism and instrument package (not shown in FIGS. 5, 6 and 7) is coupled to each outer surface 344 and 346. Surfaces 350 and 352 define dihedral angle 334 therebetween. Also, at least one push chain roller bearing 366 is coupled to inner surfaces 350 and 356 such that surfaces 350 and 356 define dihedral angle 340 therebetween. Further, roller bearings 366, in conjunction with surfaces 350 and 356, define a push chain alignment channel 368. Alternatively, devices that include, but are not limited to, chain sprockets and sleeve bearings in addition to or in lieu of bearings 366.

Also, in the exemplary embodiment, support duct 324 includes a brush and flap seal 370 that are coupled to axially innermost portions of inner surfaces 350, 352, 354, and 356. Seal 370 facilitates non-pressure-tight sealing with outer telescoping tube 310. Moreover, support duct 324 includes a plurality of over-travel stops 372 that facilitate preventing outer telescoping tube 310 from in advertently disengaging from support duct 324. In the exemplary embodiment, support duct 324 includes a first over-travel stop 372 at an axially innermost portion of inner surfaces 350 and 352, where surfaces 350 and 352 define dihedral angle 338 therebetween, a second over-travel stop 372 at an axially innermost portion of inner surfaces 352 and 354, where surfaces 352 and 354 define dihedral angle 336 therebetween, and a third over-travel stop 372 at an axially innermost portion of inner surfaces 354 and 356, where surfaces 354 and 356 define dihedral angle 334 therebetween. Alternatively, support duct 324 includes any number of over-travel stops 372 that enables operation of device 300 as described herein.

Figure 8:
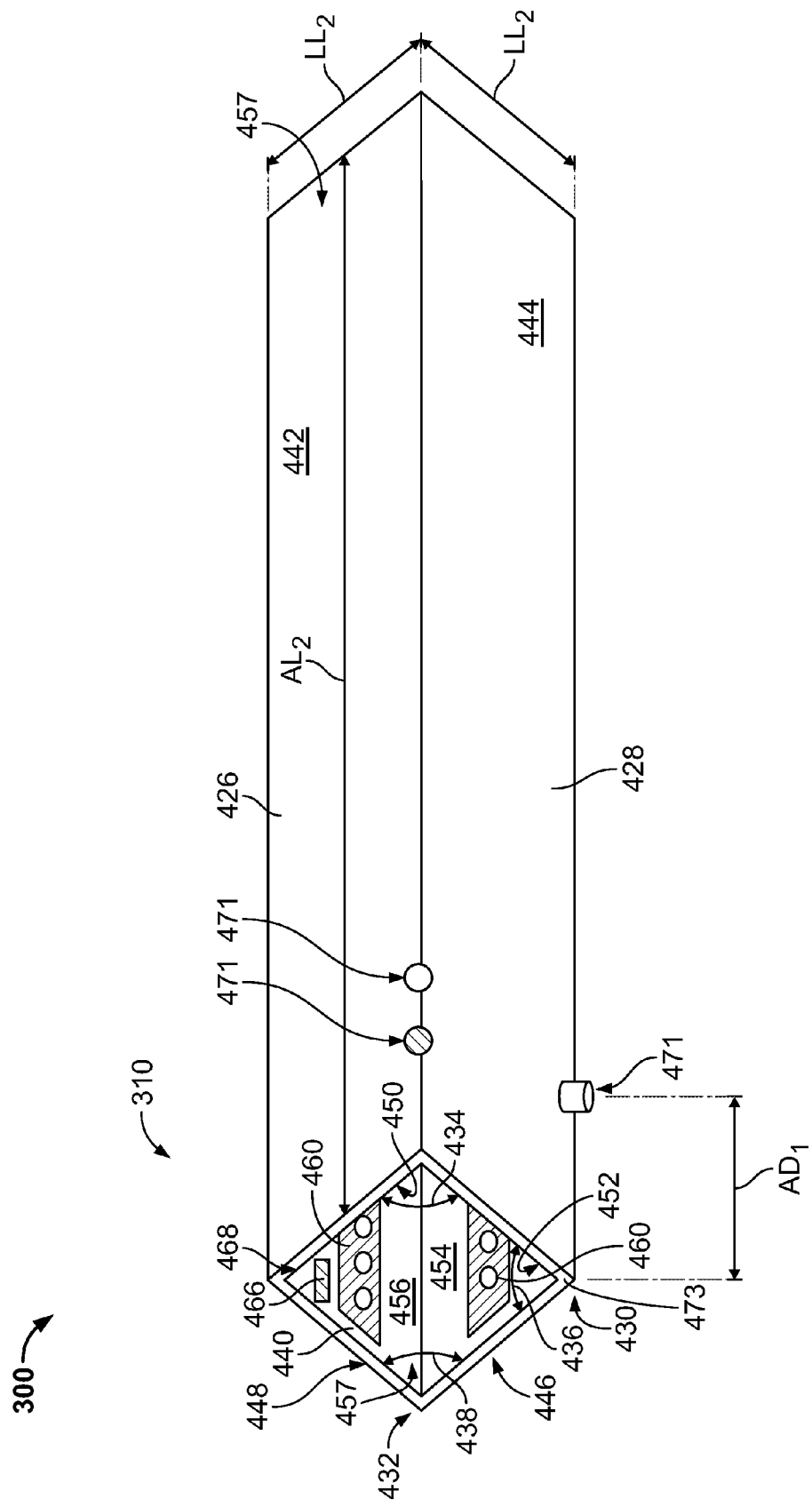
FIG. 8 is a schematic perspective view of an exemplary outer telescoping tube that may be used with the sampling probe transport device shown in FIGS. 3 and 4.
Figure 9:
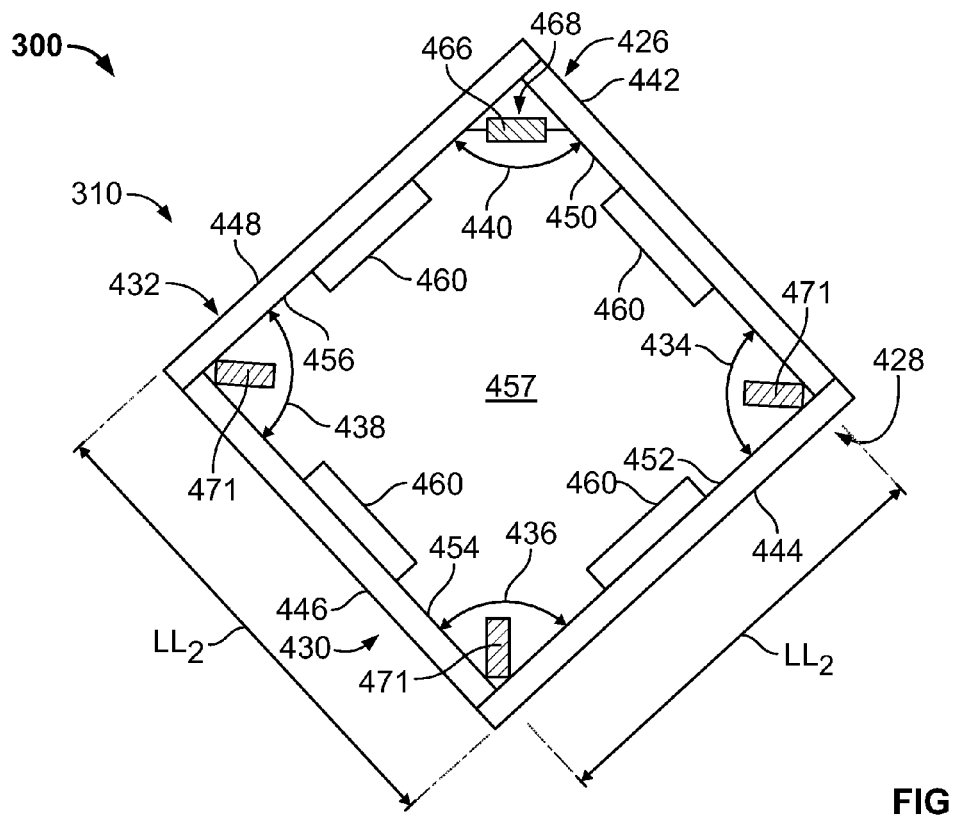
FIG. 9 is a first schematic axial view of the outer telescoping tube shown in FIG. 8.
Figure 10:
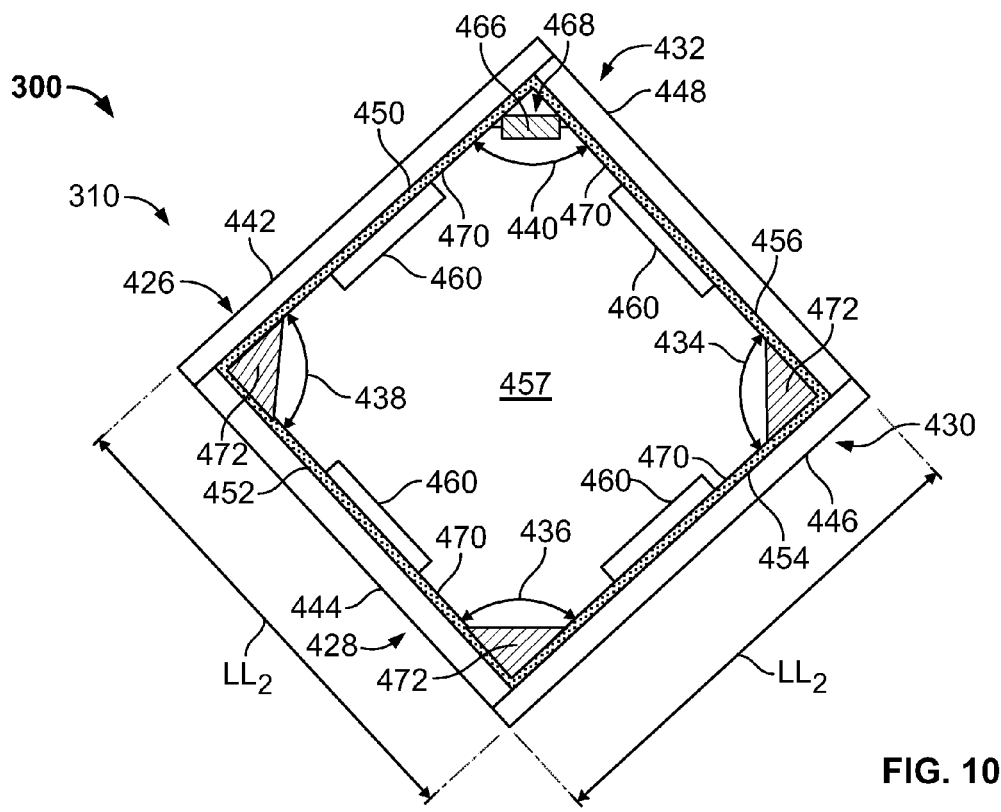
FIG. 10 is a second schematic axial view of the outer telescoping tube shown in FIG. 8.

FIG. 8 is a schematic perspective view of outer telescoping tube 310. FIG. 9 is a first schematic axial view of outer telescoping tube 310. FIG. 10 is a second schematic axial view of outer telescoping tube 310. In the exemplary embodiment, tube 310 includes four substantially identical sides 426, 428, 430, and 432. Tube 310 was a substantially square cross-sectional shape, and sides 426, 428, 430, and 432 have substantially similar dimensions that facilitate being received by support duct 324 within cavity 357 (both shown in FIGS. 5, 6, and 7). Specifically, each side 426, 428, 430, and 432 defines a longitudinal length $LL_2$ that corresponds to support tube 324 and associated longitudinal length $LL_1$ (both shown in FIG. 5). In exemplary embodiment, longitudinal length $LL_2$ is shorter than longitudinal length $LL_1$. Moreover each side 426, 428, 430, and 432 has an axial length $AL_2$ that facilitates providing cantilevered support of device 300 when it is fully extended. Moreover, in the exemplary embodiment, sides 426, 428, 430, and 432 define four substantially equal dihedral angles 434, 436, 438, and 440 of approximately 90° each. Alternatively, tube 310 has a rhomboid cross-sectional shape and angles 434, 436, 438, and 440, and dimensions $LL_2$ and $AL_2$ have any values that enable operation of device 300 as described herein.

Further, in the exemplary embodiment, each side 426, 428, 430, and 432 defines an outer surface 442, 444, 446, and 448, respectively, and an inner surface 450, 452, 454, and 456 respectively. Surfaces 450, 452, 454, and 456 define a cavity 457 that is sized to receive inner telescoping tube 312 (shown in FIGS. 3 and 4) therein. A ball bearing strip 460 is coupled to each inner surface 450, 452, 454, and 456, such that each strip 460 is slidingly coupled to an opposing outer surface (not shown in FIGS. 8, 9, and 10) of inner telescoping tube 312. Alternatively, sliding engagement of surfaces 450, 452, 454, and 456 with opposing outer surfaces of inner tube 312 is accomplished via any other fastening method that enables operation of device 300 as described herein including, but not limited to, ball bearing configurations, roller strips, and/or friction-resistant tapes and coatings. Also, at least one push chain roller bearing 466 is fixedly coupled to inner surfaces 450 and 456. Such that surfaces 450 and 456 define dihedral angle 440. Further, roller bearings 466, in conjunction with surfaces 450 and 456, define a push chain alignment channel 468.

Also, in the exemplary embodiment, tube 310 includes a brush and flap seal 470 that is coupled to axially innermost portions of inner surfaces 450, 452, 454, and 456. Seal 470 facilitates non-pressure tight air leakage sealing with inner telescoping tube 312. Moreover, tube 310 includes a plurality of over-travel tabs 471 located at an axially intermediate distance $AD_1$ from left-hand side 473 of tube 310 to facilitate preventing outer telescoping tube 310 from disengaging from support duct 324. Specifically, in the exemplary embodiment, tube 310 includes a first over-travel tab 471 at inner surfaces 450 and 452, where surfaces 450 and 452 define dihedral angle 438 therebetween, a second over-travel tab 471 where surfaces 452 and 454 define dihedral angle 436 therebetween, and a third over-travel tab 471 where surfaces 454 and 456 define dihedral angle 434 therebetween. Alternatively, tube 310 includes any number of over-travel tabs 471, in any location that enables operation of device 300 as described herein.

Further, in the exemplary embodiment, tube 310 includes a plurality of over-travel stops 472 that facilitate preventing outer telescoping tube 410 from disengaging from support duct 324. In the exemplary embodiment, tube 310 includes a first over-travel stop 472 at axially innermost portions of inner surfaces 450 and 452, where surfaces 450 and 452 define dihedral angle 438 therebetween, a second over-travel stop 472 at axially innermost portions of inner surfaces 452 and 454, where surfaces 452 and 454 define dihedral angle 436 therebetween, and a third over-travel stop 472 at axially innermost portions of inner surfaces 454 and 456, where surfaces 454 and 456 define dihedral angle 434 therebetween. Alternatively, tube 310 includes any number of over-travel stops 472 that enables operation of device 300 as described herein.

Figure 11:
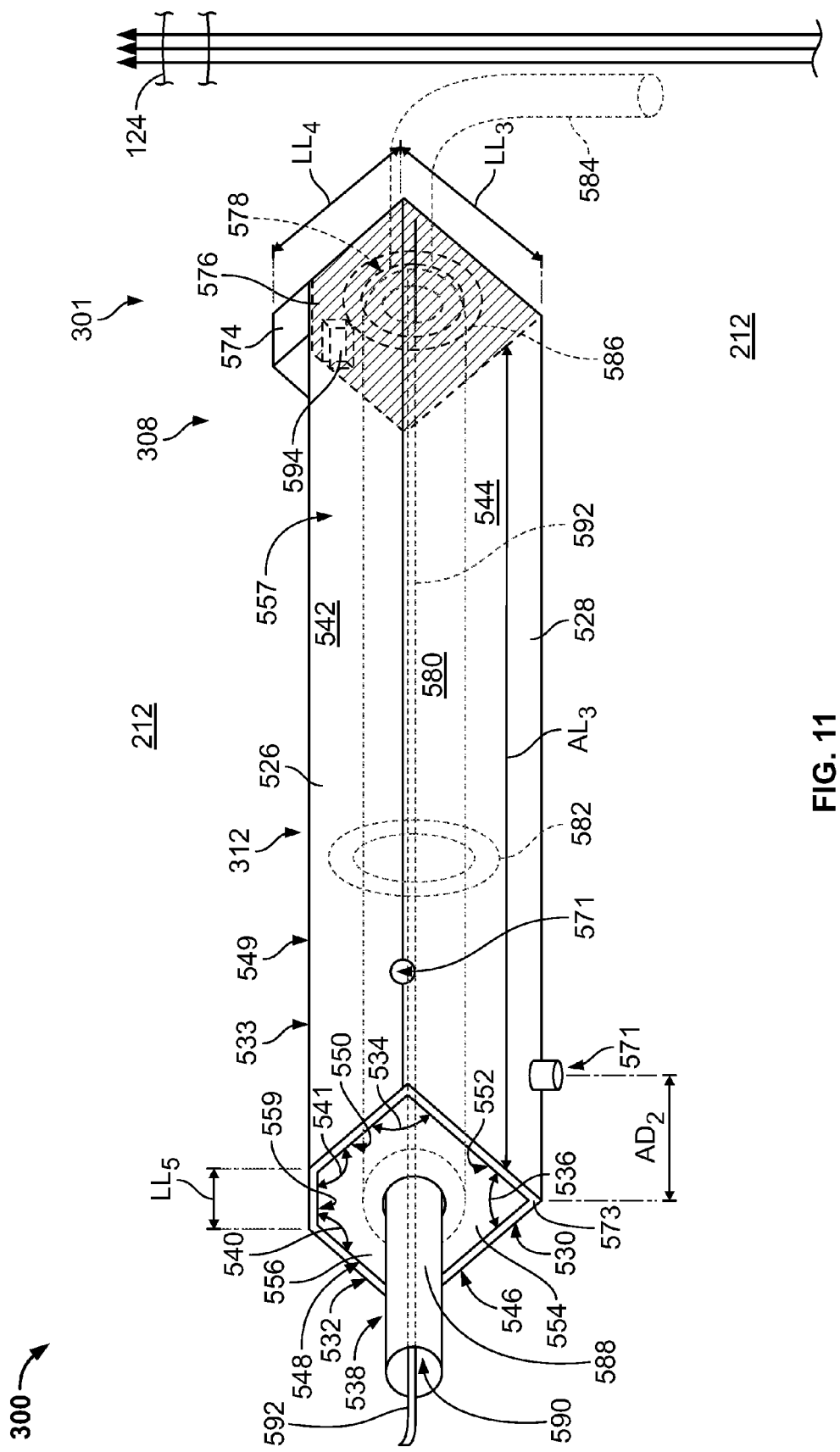
FIG. 11 is a schematic perspective view of an exemplary inner telescoping tube and an exemplary probe segment that may be used with the sampling probe transport device shown in FIGS. 3 and 4.

FIG. 11 is a schematic perspective view of inner telescoping tube 312 and probe segment 308. In the exemplary embodiment, tube 312 includes five sides 526, 528, 530, 532, and 533. Sides 526 and 532 are substantially similar to each other, and sides 528 and 530 are substantially similar to each other. Tube 312 is received by outer telescoping tube 310 within cavity 457 (both shown in FIGS. 8, 9, and 10). Specifically, sides 526 and 532 each have a longitudinal length $LL_3$ that is shorter than longitudinal length $LL_2$ (shown in FIG. 8). Also, specifically, sides 528 and 530 each have a longitudinal length $LL_4$ that is shorter then longitudinal length $LL_3$. Further, specifically, side 533 has a longitudinal length $LL_5$ that is shorter then longitudinal length $LL_4$. Moreover each side 526, 528, 530, and 532 has an axial length $AL_3$ that facilitates providing cantilevered support of device 300 when it is fully extended. Therefore, in the exemplary embodiment, sides 526, 528, 530, and 532 define three substantially equal dihedral angles 534, 536, and 538. Also, in the exemplary embodiment, sides 532, 533, and 526 define two substantially equal dihedral angles 540 and 541 of approximately 135° each. Alternatively, tube 312 is any shape, and angles 534, 536, 538, 540, and 541 and dimensions $LL_3$, $LL_4$, $LL_5$, and $AL_3$ have any values that enable operation of device 300 as described herein.

Further, in the exemplary embodiment, each side 526, 528, 530, 532, and 533 defines an outer surface 542, 544, 546, 548, and 549, respectively, and an inner surface 550, 552, 554, 556, and 559, respectively. Surfaces 550, 552, 554, 556, and 559 define a cavity 557 that is sized to receive probe components therein, as described further below. Outer surface 549 is substantially planar to facilitate operation of a push chain (not shown in FIG. 11). Moreover, tube 312 includes a plurality of over-travel tabs 571 located at an axially intermediate distance $AD_2$ from a left-hand side 573 of tube 312 that facilitate preventing inner telescoping tube 312 from disengaging from outer telescoping tube 310. Specifically, in the exemplary embodiment, tube 312 includes a first over-travel tab 571 (not shown) at inner surfaces 550 and 552, where surfaces 550 and 552, define dihedral angle 538, a second over-travel tab 571, where surfaces 552 and 554 define dihedral angle 536, and a third over-travel tab 571 where surfaces 554 and 556 define dihedral angle 534. Alternatively, tube 312 includes any number of over-travel tabs 571 located in any location that enables operation of device 300 as described herein.

Also, in the exemplary embodiment, tube 312 includes a push chain coupling device 574 that facilitates coupling a push chain to tube 312. Further, in the exemplary embodiment, tube 312 includes an end plate 576 that defines a drive shaft port 578.

Moreover, in the exemplary embodiment, tube 312 at least partially encloses probe segment 308 within cavity 557. In the exemplary embodiment, probe segment 308 includes a rigid member 580. More specifically in the exemplary embodiment, a rigid drive shaft 580. At least one support bearing 582 extends about shaft 580 and is coupled to at least a portion of shaft 580 and to at least a portion of at least one of inner surfaces 550, 552, 554, 556, and 559 such that bearing 582 facilitates radial and axial alignment of shaft 580. Struts (not shown) may also be used to facilitate such support. At least a portion of shaft 580 extends through port 578.

In addition, in the exemplary embodiment, probe segment 308 includes a sample tube 584 that is rotatably coupled to shaft 580, such that sample tube 584 receives portions of exhaust fluid stream 124. Sample tube 584 channels samples of stream 124 to apparatus (not shown) external to stack 200 for analyses that include, but art not limited to, constituent makeup, temperatures, and velocities of stream 124. Tube 312 also includes at least one sealing device, a support device, and/or a coupling device. Specifically, in the exemplary embodiment, tube 312 includes a combined tube sealing, support, and a coupling device 586 that facilitates reducing flow communication between cavity 557 and exhaust conduit 212, and that facilitates radial and axial support of shaft 580. Moreover, device 586 also facilitates coupling sample tube 584 to shaft 580. Alternatively, cavity 557 is sealed from conduit 212, shaft 580 is supported, and/or tube 584 and shaft 580 are coupled in any manner that enables operation of device 300 as described herein.

Also, in the exemplary embodiment, a flexible drive shaft 588 is rotatable coupled to shaft 580 and to a drive mechanism (not shown in FIG. 11), wherein the drive mechanism is any device that induces a rotational force on shaft 588. Shaft 588 is substantially hollow and includes a cavity 590 defined therein. Further, in the exemplary embodiment, device 300 includes a sample conduit 592 that extends from a sample collection and analysis system (not shown) through cavity 590, and through shaft 580 to sample tube 584. Moreover, in the exemplary embodiment, tube 312 includes a coaxial rotary position encoder 594 that facilitates determination of the rotational position of rigid shaft 580, and therefore, an orientation of sample tube 584. Encoder 594 is associated with rotatable elements (not shown) that are coupled to shaft 580 and a control system (not shown in FIG. 11).

Figure 12:
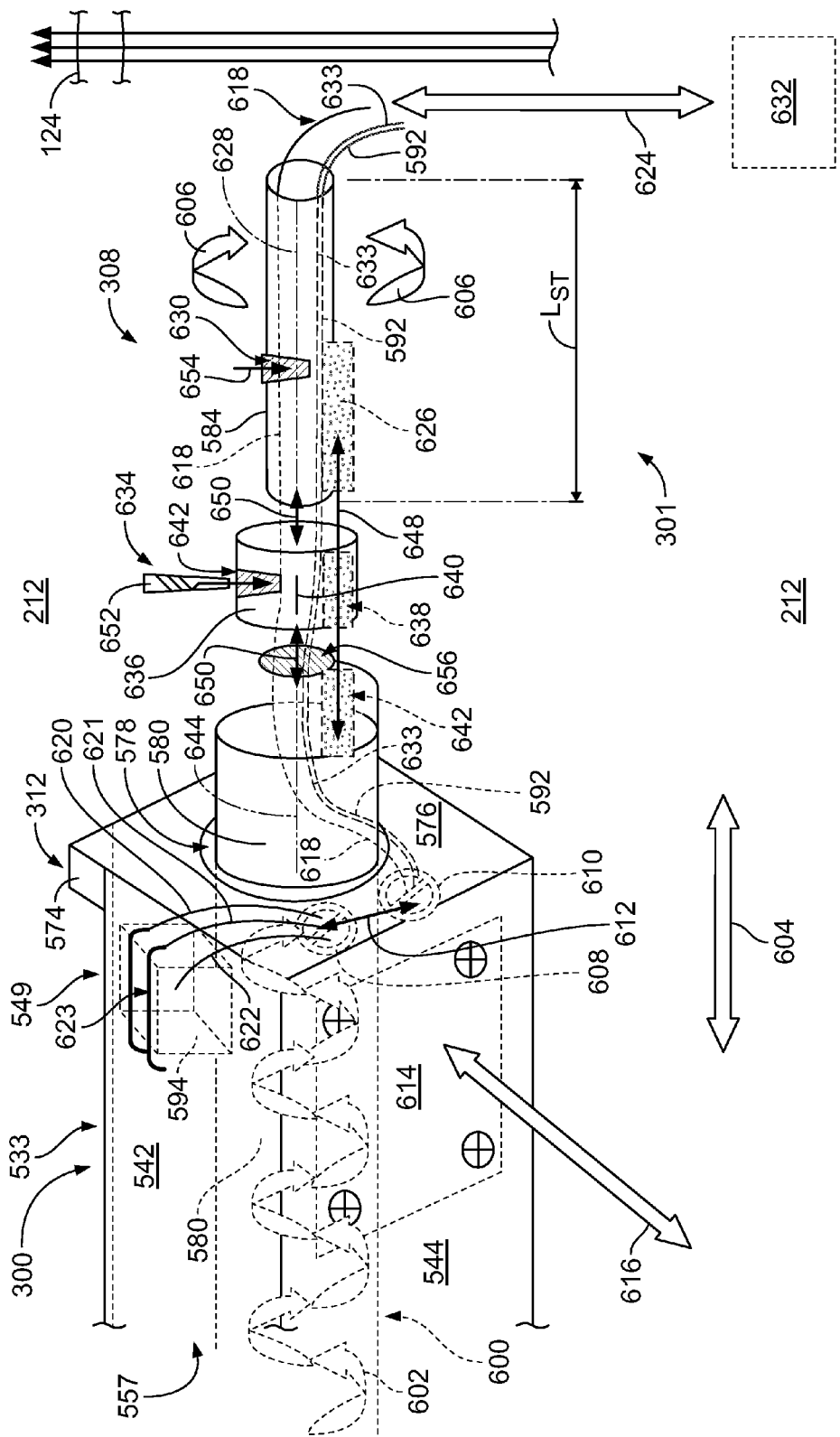
FIG. 12 is a schematic enlarged perspective view of a portion of the inner telescoping tube and the probe segment that may be used with the sampling probe transport device shown in FIGS. 3 and 4.

FIG. 12 is a schematic enlarged perspective view of a portion of inner telescoping tube 312 and probe segment 308 that may be used with sampling probe transport device 300. In the exemplary embodiment, device 300 includes a multi-function umbilical connector 600 that, in the exemplary embodiment, facilitates a variety of services including, but not limited to, transmitting sensing signals from probe segment 308 and transmitting position signals from encoder 594 to an instrument module (not shown) that is external to stack 200 (shown in FIGS. 2, 3, and 4). Moreover, connector 600 also facilitates channeling closed loop cooling air (not shown) to coaxial drive shaft position encoder 594, and channel in exhaust fluid stream samples via sample conduit 592 to the sample collection and analysis system (not shown). Moreover, umbilical connector 600 facilitates transmitting and/or channeling a variety of services between probe segment 308 and other components and external sources and systems, thereby extending the utility and useful life of such probe segment 308 and other components through an extended number of telescoping/retracting cycles of device 300.

Specifically, in the exemplary embodiment, umbilical connector 600 includes a helical coil 602 that is routed through rigid drive shaft 580. Alternatively, coil 602 is routed externally about shaft 580. Regardless, coil 602 facilitates axial movement of device 300 as indicated by axial bi-directional arrow 604, and rotational movement of probe segment 308 as indicated by rotational bi-directional arrows 606. Umbilical connector 600 also includes an umbilical connector harness 608 that couples to a probe harness 610 as indicated by arrow 612. Inner telescoping segment 312 includes an access door 614 that is removably coupled to outer surface 554 as indicated by bi-directional arrow 616. Access door 614 provides access to harnesses 608 and 610, and thereby facilitating ease of connection and disconnection of harnesses 608 and 610. Also, specifically, in the exemplary embodiment, in addition to sample conduit 592, harness 610 houses a plurality of probe signal wires 618. Moreover, in the exemplary embodiment, coil 602 houses a rigid drive shaft position encoder cooling air supply conduit 620, a rigid drive shaft position encoder cooling air return conduit 621, and a plurality of rigid drive shaft position signal wires 622. Conduits 620 and 621 and wires 622 are coupled to coil 602 via any method that enables operation of device 300 as described herein including, but not limited to, additional harnesses and/or direct insertion via slots defined in coil 602. Also, alternatively, any services, including, but not limited to, cooling air channeling, signal transmission, and sample channeling are facilitated via coil 602 via any method that enables operation of device 300 as described herein.

Cooling air supply conduit 620 and cooling air return conduit 621 are coupled in flow communication with an external cooling air source (not shown) and a plurality of cooling coils 623. In the exemplary embodiment, coils 623 are fabricated from copper. Alternatively, coils 623 are fabricated from any materials that enable operation of device 300 as described herein. Also, in the exemplary embodiment, the cooling air system is a closed loop system that facilitates reducing a potential for introducing diluting air into exhaust conduit 212 and stream 124.

Also, in the exemplary embodiment, probe segment 308 includes sample tube 584. Sample tube 584 houses sample conduit 592 and probe signal wires 618. Sample tube 584 includes a key 626 that is coupled thereto, a scribe line 628 indelibly inscribed thereon, and a set screw passage 630 defined therein. Probe segment 308 also includes a modular sensing and sampling device 632. In the exemplary embodiment, device 632 is any sensing and sampling device that enables operation of device 300 as described herein, and that senses characteristics of, and samples constituents of, stream 124 including, but not limited to, temperatures, pressures, carbon dioxide concentrations, carbon monoxide concentrations, oxygen concentrations, sulfur oxides ($SO_x$) concentrations, nitrogen oxides ($NO_x$) concentrations, moisture concentrations, particulate constituents and concentrations, and/or angular velocity vectors of stream 124 in two-dimensional and/or three-dimensional profiles, as a function of distance of insertion of sensing and sampling device 632 within conduit 212. Wires 618 are removably coupled to device 632 as indicated by bi-directional arrow 624 in any manner that enables operation of device 300 as described herein. Sample tube 584 has a length $L_{ST}$ that facilitates reducing in turbulence induced in the vicinity of device 632 by telescoping tubes 310 and 312, while also providing cantilevered support of device 300 as described herein. Moreover, sample tube 584 has any size, shape, orientation, and/or configuration that enables operation of device 300 as described herein.

Further, in the exemplary embodiment, probe segment includes a pressure sensing conduit 633 that facilitates measuring a pressure of fluid stream 124. Coil 602 houses pressure sensing conduit 633 that is formed from any extendible material and has any size, orientation, and/or configuration that enables operation of device 300 as described herein. Conduit 633 is coupled in flow communication with at least one pressure transducer (not shown) external to stack 200.

Moreover, in the exemplary embodiment, probe segment 308 is removably coupled to inner telescoping segment 312 via a coupling device 634. In the exemplary embodiment, coupling device 634 is a collar-type device. Alternatively, device 634 is any type of coupling device that enables operation of device 300 as described herein. Device 634 includes a collar 636 that includes a key passage 638 defined therein, an optional scribe line 640 inscribed thereon, and a set screw passage 642 defined therein. Also, in the exemplary embodiment, to facilitate coupling rigid drive shaft 580 and sample tube 584 via coupling device 634 in a manner that facilitates reducing fluid communication between cavity 557 and conduit 212, shaft 580 includes a key passage 642 defined therein and a scribe line 644 inscribed thereon.

Therefore, in the exemplary embodiment, sample tube 584 is removably coupled to shaft 580 when key 626 is inserted through key passages 638 and 642 such that scribe lines 628, 640, and 644 are substantially linearly aligned, and after at least one set screw 652 is inserted into each of set screw passages 630 and 642. Sample conduit 592 and probe signal wires 618, including harness 576, are inserted into cavity 557 through sample tube 584.

As described above, tube 312 includes coaxial rotary position encoder 594 that is associated with a control system (not shown in FIG. 12). Encoder 594 facilitates determining a rotational position of rigid shaft 580, and therefore, an orientation of device 632, and is associated with rotatable elements (not shown) coupled to shaft 580. As shaft 580 is rotated, device 632 is also rotated. Since device 632 is securely coupled to shaft 580, encoder 594 generates and transmits an accurate rotational position feedback signal to the rotational control system. In the exemplary embodiment, encoder 594 is initially aligned to plumb, i.e., substantially vertical, such that dihedral angles 334-340 (shown in FIGS. 5, 6, and 7), 434-440 (shown in FIGS. 8, 9, and 10), and 534-538 (shown in FIG. 11) are substantially aligned with plumb during assembly of device 300 using methods that include, but are not limited to, the use of plumb bobs, to attain a predetermined alignment of tubes 310 and 312 with fixed segment 304 and probe segment 308.

Figure 13:
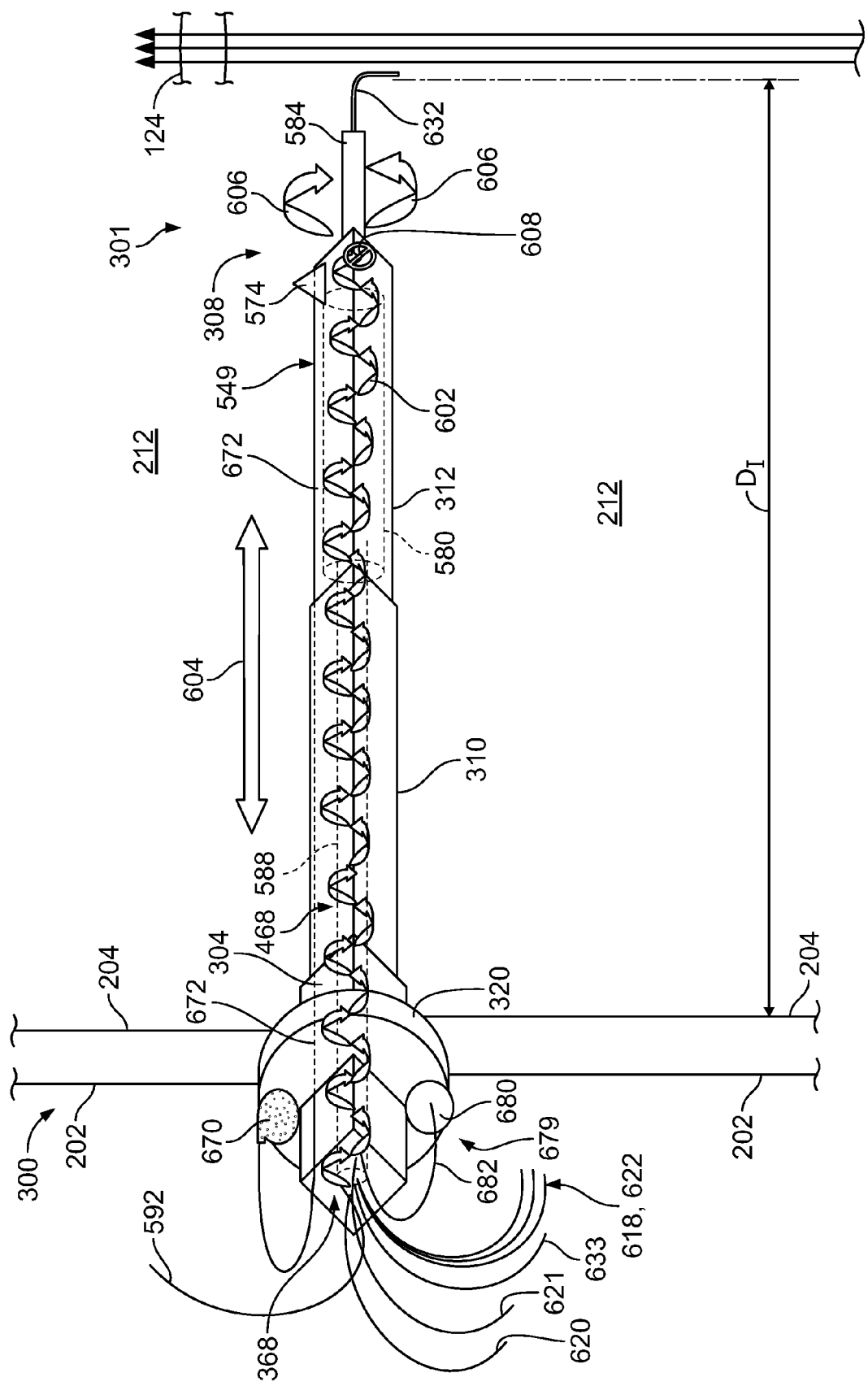
FIG. 13 is a schematic perspective view of the sampling probe transport device shown in FIG. 3 in an extended position.

FIG. 13 is a schematic perspective view of sampling probe transport device 300 in an extended position. In the exemplary embodiment, device 300 includes a push chain winch 670 coupled to fixed segment 304 via mounting pads 358 (shown in FIGS. 5, 6, and 7), and a push chain 672 extending from winch 670 for use in positioning chain coupling device 574 via alignment channels 368 and 468, and surface 549. Winch 670, chain 672, channels 368 and 468, and surface 549 cooperate to extend and retract device 300 through exhaust conduit 212. In the exemplary embodiment, drive forces to induce extension and retraction of device 300 via push chain winch 670 are generated by an electric motor (not shown). Alternatively, any drive device that enables operation of device 300 as described herein is used including, but not limited to, pneumatic drives, hydraulic drives, and hand-operated drives.

Coil 602 facilitates axial movement of device 300 as indicated by axial bi-directional arrow 604 and rotational movement of probe segment 308 as indicated by rotational bi-directional arrows 606. Moreover, coil 602 reduces a potential for coil fouling, or more specifically, coil 602 facilitates avoidance of interference with components proximate to flexible drive shaft 588 and rigid drive shaft 580 during extending and retracting device 300 axially within exhaust conduit 212. In the exemplary embodiment, coil 602 is routed circumferentially about flexible drive shaft 588 and within rigid drive shaft 580, such that coil 602 extends from shaft 588 into shaft 580 via a slot (not shown). Alternatively, coil 602 is routed within shaft 588.

Also, in the exemplary embodiment, device 300 includes a rotary positioning mechanism and instrument package 679, or more specifically, a rotary drive device 680 that is coupled to fixed segment 304 via mounting pads 362 (shown in FIGS. 5, 6, and 7), and a rotary drive cable 682 that is coupled to flexible drive shaft 588. Package 679, and therefore devices 680 and 682, are associated with a control system (not shown in FIG. 13) and cooperate to independently rotate probe segment 308 through a full 360° relative to radially fixed tubes 310 and 312. Rotary drive 680 is any drive device that enables operation of device 300 as described herein including, but not limited to, an electric motor, a pneumatic drive, a hydraulic drive, and a hand-operated drive.

In the exemplary embodiment, control of extension positioning of device 300, including automatic stopping of extension and retraction at specific lengths, such as, but not limited to, full extension and full retraction is performed and a distance of immersion $D_I$ of modular sensing and sampling device 632 into exhaust fluid stream 124 within exhaust conduit 212 is determined with a control system (not shown in FIG. 13) as discussed further below.

In operation, push chain winch 670 is operated to extend push chain 672 through push chain alignment channels 368 and 468. Push chain roller bearings 366 and 466 and outer surface 549 facilitate aligning chain 672, as such that chain 672 induces an axially outward force on push chain coupling device 574. Device 574 thereby induces an outward force on inner telescoping tube 312 and probe segment 308 such that tube 312 and probe segment 308 extend into stream 124 within conduit 212. Brush and flap seal 470 cooperate to provide non-pressure-tight sealing with inner telescoping tube 312 during extension and retraction operations.

Also, during operation, as tube 312 extends into stream 124, ball bearing strips 460 slidingly engage surfaces 542, 544, 546, and 548 to cause movement of tube 312 within cavity 457 until over-travel tabs 571 contact over-travel stops 472. Subsequently, tube 310 extends into stream 124, thereby further extending tube 312 and probe segment 308 into stream 124. As tube 310 extends into stream 124, ball bearing strips 360 slidingly engage surfaces 442, 444, 446, and 448 to cause movement of tube 310 within cavity 357 until over-travel tabs 471 contact over-travel stops 372, wherein device 300 is fully extended into stream 124, and winch 670 automatically stops. Brush and flap seal 370 cooperate to create non-pressure tight air leakage sealing with outer telescoping tube 310 during extension and retraction operations.

Extending device 300 into stream 124 may induce a drooping effect on device 300 as a function of a length of extension. Droop of device 300 may affect a sampling accuracy of stream 124. The shape of device 300 facilitates longitudinal alignment and axial rigidity of device 300. More specifically, for example, sides 528 and 530 slidingly engage sides 428 and 430 and sides 428 and 430 slidingly engage sides 328 and 330. Also, lengths $LL_3$, $LL_2$, and $LL_1$ are selected to enable sliding engagement of associated tubes 310 and 312 and segment 304, as well as to ensure sufficient contact to facilitate rigidity and cantilevered support as device 300 is extended into stream 124. Enhancing the rigidity of device 300 facilitates reducing a potential for device 300 to droop when extended into stream 124. In some embodiments, upward draft forces associated with stream 124 may further facilitate reducing a potential for droop of device 300.

Further, in operation, a control system (not shown in FIG. 13) determines a distance of immersion $D_I$ of modular sensing and sampling device 632 into exhaust fluid stream 124. Distance $D_I$ is variable and is determined either by an operator or via scheduled programming wherein distance $D_I$ is any extension of sampling device 632 into stream 124, up to and including, full extension of device 300.

Moreover, in operation, rotary drive device 680 and rotary drive cable 682 rotate flexible drive shaft 588 to cause rotation of rigid drive shaft 580. Drive shaft 580 rotates probe segment 308, including sampling device 632, to a predetermined orientation with respect to stream 124. Rotary position encoder 594 determinates a rotational position of rigid shaft 580, and therefore, an orientation of sampling device 632 with respect to stream 124.

Also, in operation, after completion of sampling activities, push chain winch 670 is operated to retract push chain 672 through push chain alignment channels 368 and 468, using push chain roller bearings 366 and 466 and outer surface 549 to facilitate alignment of chain 672, such that chain 672 induces an inward force on push chain coupling device 574. Device 574 thereby induces an inward force on inner telescoping tube 312 and exemplary probe segment 308 such that tube 312 and probe segment 308 retract from stream 124. As tube 312 axially retracts, it engages tube 310, and tube 310 starts to retract, until device 300 is fully retracted and winch 670 automatically stops.

FIG. 14 is a schematic cross-sectional view of an alternative sampling probe transport device 700, in a retracted position, that may be used with exhaust stack 200. FIG. 15 is a schematic cross-sectional view of sampling probe transport device 700 shown in an extended position. In this alternative embodiment, device 700 and at least one probe segment 308 are assembled to form a fluid sampling device 701. Device 700 extends and retracts, i.e., transports probe segment 308 within exhaust stack 200 as indicated by axial arrow 702. Also, device 700 automatically controls and measures an insertion depth $D_I$ and a rotation of probe segment 308 within exhaust stack 200 as indicated by arrow 704. Further, device 700 facilitates automation of sampling and velocity traverse of exhaust fluid stream 124 (shown in FIGS. 1 through 4 and 11 through 13) in exhaust stack 200.

In the exemplary embodiment, device 700 includes an axial extension and retraction assembly 708. More specifically, in the exemplary embodiment, assembly 708 is a slide track that includes at least one slidable surface 710 and a carriage 712. Carriage 712 includes a first portion 714 that is positioned above slidable surface 710, and a second portion 716 that is slidably coupled to at least a portion of slidable surface 710.

Carriage 712 moves axially along slide track 708 as indicated by axial arrow 718. In the exemplary embodiment, carriage 712 is a pneumatic drive device 720 that includes a first fluid conduit 722 that is coupled in flow communication with a fluid source 724 and with carriage first portion 714. Also, in the exemplary embodiment, device 720 includes a second fluid conduit 726 that is coupled in flow communication with slide track 708 and with fluid source 724. As such, device 720 uses an air-slide effect that facilitates extended position control of probe segment 308 along distance $D_I$. Further, in the exemplary embodiment, conduits 722 and 726 are flexible and/or extendible hoses that enable coupling during cycles of device 700. Conduits 722 and 726 are formed from any materials that enable operation of device 700 as described herein. Moreover, in the exemplary embodiment, fluid source 724 is a pressurized air source. Alternatively, fluid source 724 may be any source of fluid that enables operation of device 700 as described herein, including, but not limited to, water and hydraulic fluid.

Also, in this alternative embodiment, device 700 is independently supported by a support stand 728 and a mounting and support block 730 (described in more detail below). Alternatively, device 700 is supported by any device that enables operation of device 700 as described herein, including, but not limited to, overhead support devices, e.g., an overhead monorail system (not shown).

Alternative embodiments of sampling probe transport device 700 include, rather than, or in addition to, pneumatic drive device 720, an alternative drive device 732, such as, but is not limited to, at least one of an electrical drive device, a rack and pinion drive device, a cable drive device, and a chain drive device (all shown in phantom in FIG. 14 only) that are drivingly coupled to carriage 712, to facilitate control of a position of carriage 712. Therefore, consistent with the use of devices 720 and/or 732 within device 700, slide track 708, and slide surface 712 form at least one of a rail-type and a flat surface-type system.

In operation, carriage 712 and slide track 708 receive pressurized air from source 724 via conduits 722 and 726, respectively. An air layer is formed about surface 710 that thereby facilitates axial transport of carriage 712 parallel to arrow 718 via pneumatic drive device 720.

Figure 16:
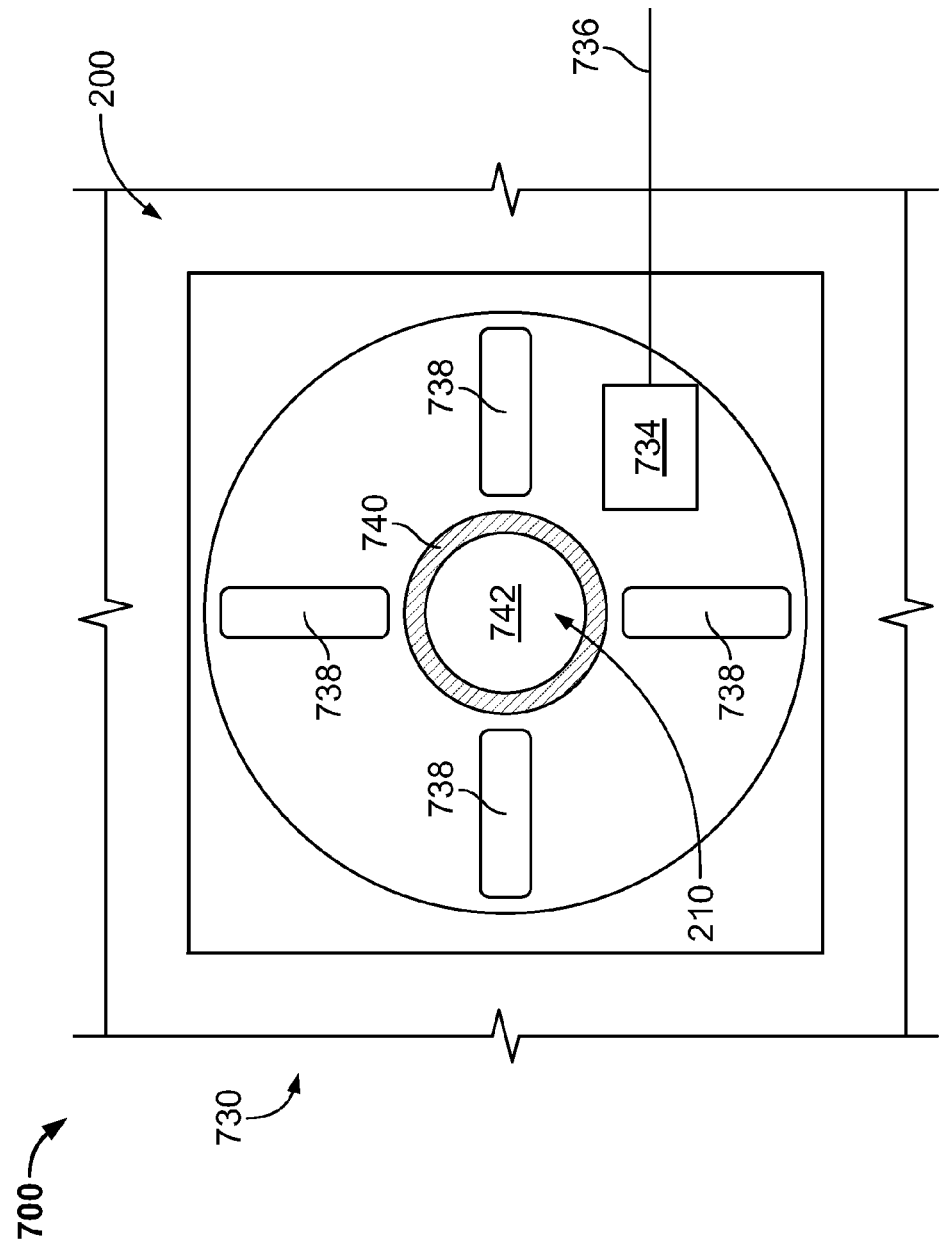
FIG. 16 is a schematic axial view of a mounting and support block that may be used with the sampling probe transport device shown in FIGS. 14 and 15.

FIG. 16 is a schematic axial view of mounting and support block 730 that may be used with sampling probe transport device 700. Support block 730 is coupled to exhaust stack 200 at exhaust fluid sampling probe port 210 via fastening hardware (not shown) that includes, but is not limited to only including bolting, and an extension flange 733 (shown in FIGS. 14 and 15). Alternatively, support block 730 is coupled to stack 200 using any devices and methods that enable operation of device 700 as described herein. Probe segment 308 (shown in FIGS. 14 and 15) is slidingly engaged with support block 730 such that support block 730 provides radial and lateral support, as well as axial and rotational positioning of probe segment 308. Moreover, support block 730 is coupled to slide track 708 (shown in FIGS. 14 and 15), thereby providing radial and lateral support of slide track 708.

In this alternative embodiment, support block 730 includes a probe segment position feedback device 734 that enables a length of probe segment 308 to measured as it extends through support block 730, thereby facilitating control of a position of carriage 712 and therefore, control of insertion depth $D_I$ (shown in FIG. 15) of probe segment 308 within exhaust stack 200. In the exemplary embodiment, device 734 is one of a friction-driven wheel sensor, an encoding sensor, and a linear position transducer. Alternatively, device 734 is any apparatus that enables operation of device 700 as described herein. Also, in the exemplary embodiment, device 734 is coupled to a control system (not shown in FIG. 16) via at least one wire and/or cable 736. Alternatively, device 734 is coupled to the control system via radio-frequency (RF) communication devices (not shown). Also, alternatively, device 734 measures rotational positions of probe segment 308. As such, device 734 is at least one of, and is not limited to only being, a rotational position encoder and a rotational position transducer.

Further, in the exemplary embodiment, support block 730 includes a plurality of fastener passages 738 that are sized and oriented to facilitate coupling of support block 730 to exhaust stack 200. Support block 730 includes, for example, but is not limited to onlt including, provisions for a variety of fastener configurations. Moreover, block 730 can be rotated to accommodate various fastener orientations. More specifically in the exemplary embodiment, support block 730 includes four fastener passages 738 that are oriented such that adjacent passages are generally orthogonal to each other. Alternatively, support block 730 may include any number of passages 738 in any orientation that enables operation of device 700 as described herein.

Moreover, in the exemplary embodiment, support block 730 includes a combination bearing and seal assembly 740. Assembly 740 includes a probe passage 742 that is in flow communication with probe port 210. Assembly 740 provides radial support of probe 308 while enabling axial motion of probe 308 through passage 742, such that insertion depth $D_I$ can be varied and probe 308 can be rotated. Also, assembly 740 facilitates reducing channeling of exhaust fluid stream 124 (shown in FIGS. 1 through 4 and 11 through 13) externally of exhaust stack 200 and device 700.

Figure 17:
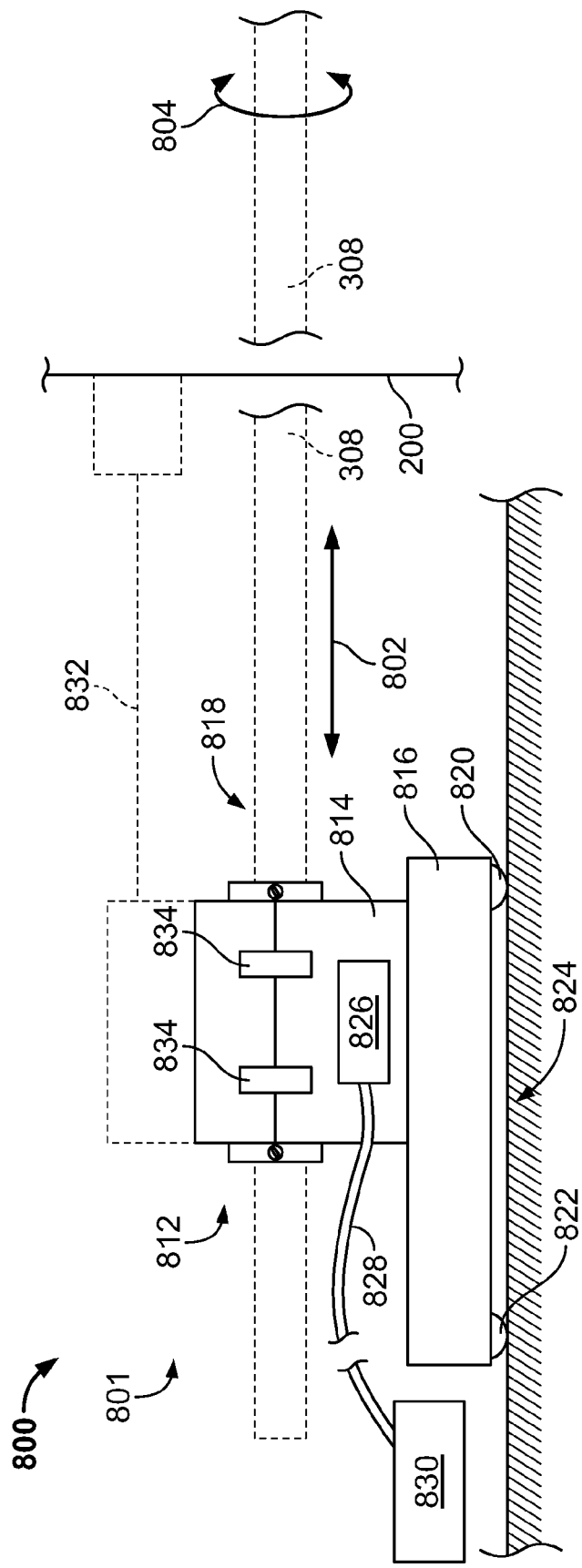
FIG. 17 is a schematic cross-sectional view of another alternative sampling probe transport device that may be used with the exhaust stack shown in FIG. 2.

FIG. 17 is a schematic cross-sectional view of another alternative sampling probe transport device 800 that may be used with exhaust stack 200. In the exemplary embodiment, device 800 and at least one probe segment 308 are assembled to form a fluid sampling device 801. Device 800 extends and retracts, i.e., transports probe segment 308 within exhaust stack 200 as indicated by axial arrow 802. Also, device 800 automatically controls and measures an insertion depth $D_I$ (shown in FIGS. 13 and 15) and a rotational orientation of probe segment 308 within exhaust stack 200 as indicated by arrow 804. Moreover, device 800 enables automation of sampling and velocity traverse of exhaust fluid stream 124 (shown in FIGS. 1 through 4 and 11 through 13) in exhaust stack 200. Moreover, probe segment 308 is slidingly coupled to support block 730 (shown in FIGS. 14, 15, and 16) such that support block 730 provides radial and lateral support, as well as axial and rotational positioning, of probe segment 308.

Also, in this alternative embodiment, device 800 includes a carriage 812. Carriage 812 includes a first portion 814 and a second portion 816 that, when coupled to each other, form an axial extension and retraction assembly. In the exemplary embodiment, carriage 812 is a motorized car 818. Car 818 includes at least one wheel 820 and/or at least one roller 822 that are positioned on a floor 824 near stack 200. In this alternative embodiment, floor 824 includes either a slide track (not shown) or a slide surface (not shown). Carriage 812 moves axially along floor 824 as indicated by axial arrow 802. In this alternative embodiment, carriage 812 includes an electric motor drive 826 that is coupled to an electrical conduit 828 that is coupled to an electrical power source 830. Also, in this embodiment, conduit 828 is a flexible and/or extendible conduit that enables coupling during cycles of device 800. Conduit 828 is formed from any material that enables operation of device 800 as described herein.

Alternatively, sampling probe transport device 800 may include, rather than or in addiction to electric motor drive 826, an alternative drive device 832, such as, but not limited to, at least one of a pneumatic drive device, a rack and pinion drive device, a cable drive device, and a chain drive device (all shown in phantom) drivingly coupled to carriage 812, to provide positional control of carriage 812. Further, in this alternative embodiment, device 800 includes a plurality of latches 834 that facilitate opening of carriage first portion 814 for inspection, repair, and replacement of components within carriage 812. More specifically, latches 834 facilitate access that further facilitates installation and removal of probe segment 308.

In operation, motorized car 818 transports itself in a direction along floor 824 that is substantially parallel to arrow 802 via electric motor drive 826.

Figure 18:
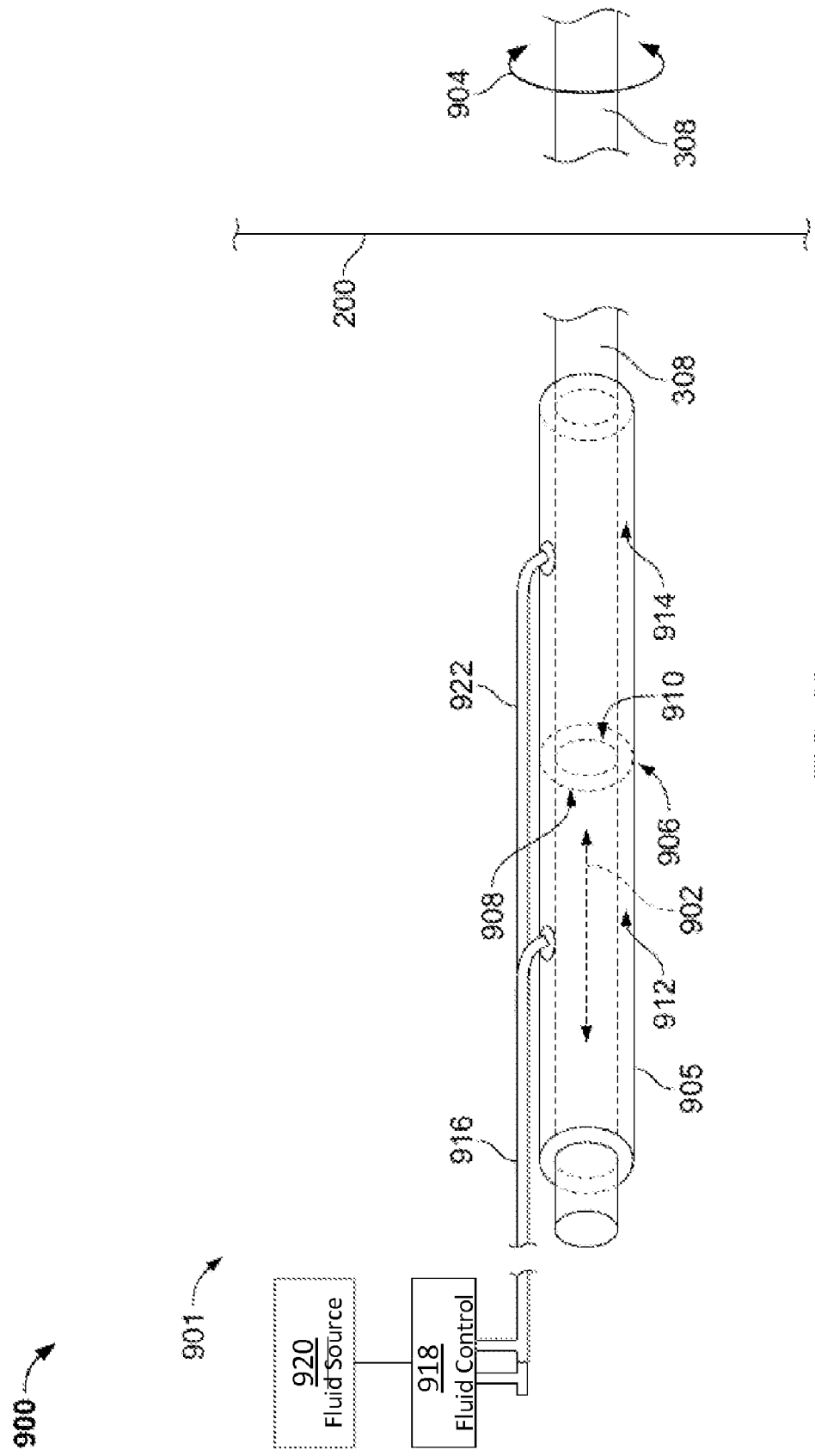
FIG. 18 is a schematic cross-sectional view of another alternative sampling probe transport device that may be used with the exhaust stack shown in FIG. 2.

FIG. 18 is a schematic cross-sectional view of another alternative sampling probe transport device 900 that may be used with exhaust stack 200. In this embodiment, device 900 and at least one probe segment 308 are assembled together to form a fluid sampling device 901. Device 900 extends and retracts, i.e., transports, probe segment 308 within exhaust stack 200 as indicated by arrow 902. Also, device 900 automatically controls and measures an insertion depth $D_I$ (shown in FIGS. 13 and 15) and a rotational position of probe segment 308 within exhaust stack 200 as indicated by rotation arrow 904. Further, device 900 facilitates automation of sampling and velocity traverse of exhaust fluid stream 124 (shown in FIGS. 1 through 4 and 11 through 13) in exhaust stack 200. Moreover, probe segment 308 is slidably coupled to support block 730 (shown in FIGS. 14, 15, and 16) such that support block 730 provides radial and lateral support, as well as axial and rotational positioning of probe segment 308.

Also, in this embodiment, device 900 is a fluid-drive device. More specifically, in the exemplary embodiment, device 900 includes a sealed enclosure 905, or casing 905 and a positioning device 906 that, when coupled together, form an axial extension and retraction assembly. Device 906, in the exemplary embodiment is a substantially annular diaphragm 906. In this alternative embodiment, enclosure 905 is substantially cylindrical and facilitates operation of device 900 with a pressurized fluid. Alternatively, enclosure 905 has any shape that enables operation of device 900 as described herein. Further, in the exemplary embodiment, diaphragm 906 is secured to probe segment 308. Moreover, diaphragm 906 is slidably coupled enclosure 905 and diaphragm 906 includes a first motive surface 908 and a second motive surface 910. Alternatively, any positioning device that enables operation of device 900 as described herein may be used.

In the exemplary embodiment, first motive surface 908, enclosure 905, and probe segment 308 at least partially define a pressure insertion cavity 912. Similarly, second motive surface 910, enclosure 905, and probe segment 308 at least partially define a pressure retraction cavity 914. Also, in the exemplary embodiment, device 900 includes a first fluid conduit 916 that is coupled in flow communication with insertion cavity 912 and with a fluid control apparatus 918. Fluid control apparatus 918 is coupled in flow communication with a fluid source 920.

Moreover, in the exemplary embodiment, device 900 includes a second fluid conduit 922 that is coupled in flow communication with retraction cavity 914 and fluid control apparatus 918. Moreover, in this alternative embodiment, the motive fluid used is pressurized air. Alternatively, any fluid that enables operation of device 900 as described herein is used, including, but not limited to, hydraulic fluid and water.

In operation, to insert probe segment 308, pressurized air is channeled to insertion cavity 912 from source 920 via control apparatus 918 and conduit 916. Because air pressure within cavity 912 is greater than air pressure in cavity 914, a motive insertion force is induced to diaphragm surface 908 and probe 308 is inserted into stack 200 in a direction that is substantially parallel to arrow 902. Also, during operation, to retract probe segment 308, pressurized air is channeled to retraction cavity 914 from source 920 via control apparatus 918 and conduit 922. Because air pressure within cavity 914 is greater than air pressure in cavity 912, a motive retraction force is induced on diaphragm surface 910 and probe 308 is retracted from stack 200 in a direction that is substantially parallel to arrow 902.

Figure 19:
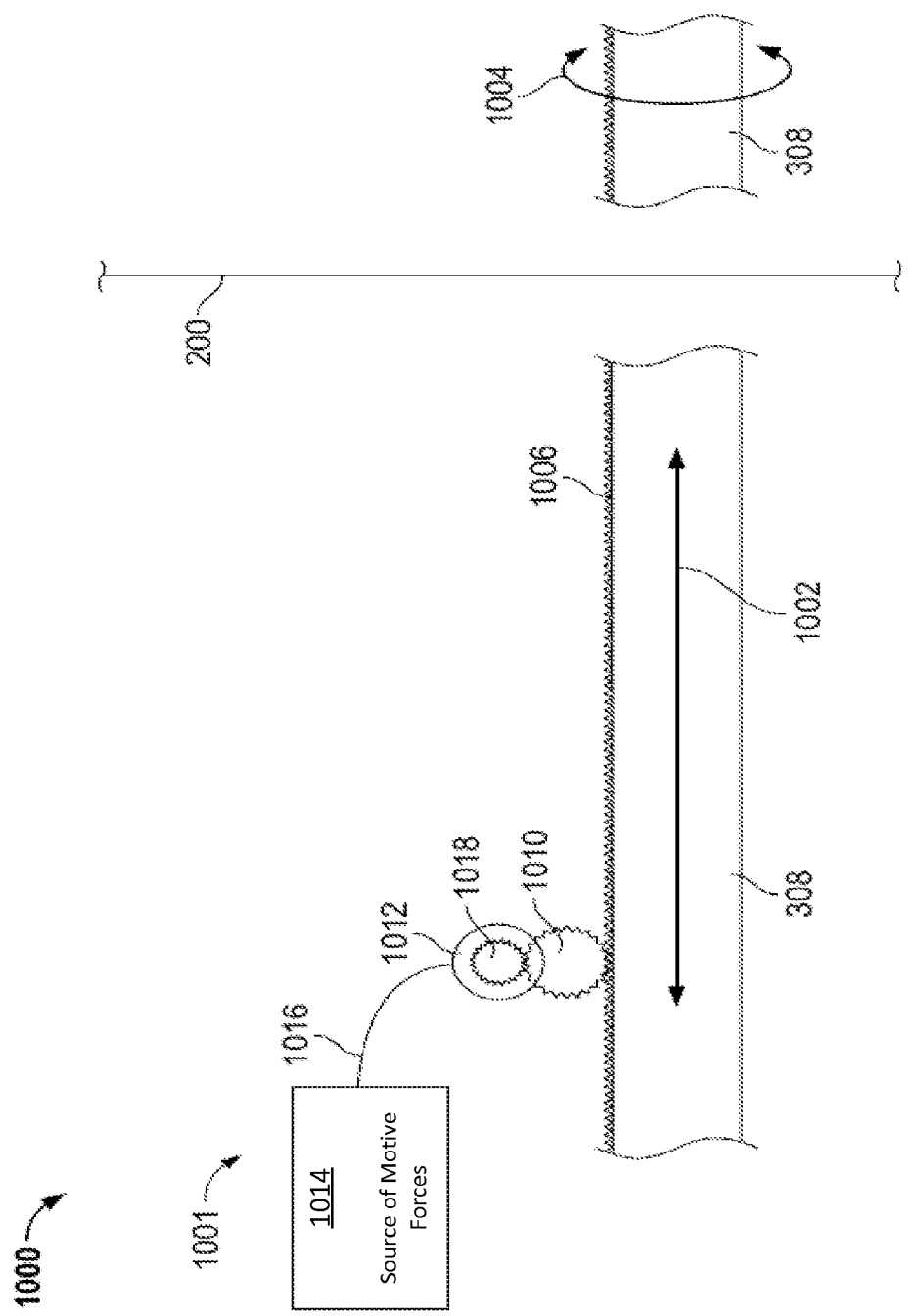
FIG. 19 is a schematic cross-sectional view of another alternative sampling probe transport device that may be used with the exhaust stack shown in FIG. 2.

FIG. 19 is a schematic cross-sectional view of another alternative sampling probe transport device 1000 that may be used with exhaust stack 200. In this embodiment, device 1000 and at least one probe segment 308 are assembled together to form a fluid sampling device 1001. Device 1000 extends and retracts, i.e., transports probe segment 308 within exhaust stack 200 as indicated by arrow 1002. In addition, device 1000 automatically controls and measures an insertion depth $D_I$ (shown in FIGS. 13 and 15) and a rotational position of probe segment 308 within exhaust stack 200 as indicated by arrow 1004. Further, device 1000 facilitates automation of sampling and velocity traverse of exhaust fluid stream 124 (shown in FIGS. 1 through 4 and 11 through 13) in exhaust stack 200. Moreover, probe segment 308 is slidably coupled to support block 730 (shown in FIGS. 14, 15, and 16) such that support block 730 provides radial and lateral support, as well as axial and rotational positioning of probe segment 308.

Also, in the exemplary embodiment, device 1000 is a rack and pinion-type apparatus that extends and retracts probe segment 308. Device 1000 includes a straight-tooth gear rack 1006 that is slidably coupled to probe segment 308. Further, in the exemplary embodiment, device 1000 includes at least one driving gear 1008 that is drivingly engaged with a driven gear 1010 that is drivingly engaged with gear rack 1006. Moreover, driving gear 1008 is rotatably coupled to a driving device 1012 that is one of an electrically-driven motor and a fluid-driven motor. Further, driving device 1012 is coupled to a source of motive forces 1014 via a conduit 1016. In the exemplary embodiment, the source of motive forces 1014 are one of an electrical power source, a hydraulic fluid source, an air source, and a water source.

In operation, to insert probe segment 308, drive device 1012 induces a clockwise rotational movement to driving gear 1008. Driving gear 1008 then induces a counter-clockwise rotational movement to driven gear 1010. Driven gear 1010 subsequently induces an insertion force to probe segment 308 via gear rack 1006. Also, during operation, to retract probe segment 308, drive device 1012 induces a counter-clockwise rotational movement to driving gear 1008. Driving gear 1008 then induces a clockwise rotational movement to driven gear 1010. Driven gear 1010 subsequently induces a retraction movement to probe segment 308 via gear rack 1006.

FIG. 20 is a schematic axial view of an alternative rotational positioning device 1100 that may be used with sampling probe transport devices 700, 800, 900, and 1000 (shown in FIGS. 14 and 15, 16, 17, and 18, respectively). FIG. 21 is a schematic cross-sectional view of rotational positioning device 1100. FIG. 22 is another schematic axial view of rotational positioning device 1100. FIG. 20 illustrates rotational device 1100 embedded in sampling probe transport device 800, however, rotational device 1100 may also be embedded within any of sampling probe transport devices 700, 900, and 1000. Device 1100 facilitates automatic control of rotation of probe segment 308 within exhaust stack 200 (shown in FIGS. 14 through 19) as indicated by arrow 1101. More specifically, device 1100 facilitates automation of sampling and velocity traverse of exhaust fluid stream 124 (shown in FIGS. 1 through 4 and 11 through 13) in exhaust stack 200.

In the exemplary embodiment, device 1100 includes a rotator ring assembly 1102. Assembly 1102 includes a center portion 1104 that is slidably coupled to two end portions 1106. Assembly 1102 also includes a plurality of set screws 1108 that couple device 1100 to probe segment 308 via end segments 1106. Alternatively, assembly 1102 includes a collar-type device (not shown) that couples device 1100 to probe segment 308.

In the exemplary embodiment, device 1100 is a rack and pinion-type apparatus. As such, device 1100 includes a toothed gear ring 1110 that is securely coupled to, and circumscribes, center portion 1104. Further, in this alternative embodiment, device 1100 includes at least one driving gear 1118 that is drivingly engaged with a driven gear 1120. Driven gear 1120 is drivingly engaged with toothed gear ring 1110. Moreover, driving gear 1118 is rotatably coupled to a driving device 1122 that is one of an electrically-driven motor and a fluid-driven motor. Further, driving device 1122 is coupled to a source of motive forces 1124 via a conduit 1126 and sources 1124 are one of an electrical power source, a hydraulic fluid source, an air source, and a water source.

Moreover, in this alternative embodiment, in addition to controlling rotation of probe segment 308, device 1100 also includes at least one bearing 1128 that provides radial and/or thrust support of probe segment 308 within sampling probe transport devices 700, 800, 900, and 1000. Also, in this embodiment, bearing 1128 provides radial and axial alignment of probe segment 308 and rotator ring assembly 1102. Further, in this alternative embodiment, probe segment 308 and bearing 1128 cooperate to form a keyed passage 1130 that receives a key 1132, thereby facilitating alignment between a zero degree position of probe segment 308 and device 1100 (shown as passage 1130). Alternatively, alignment of probe segment 308 and device 1100 is facilitated with any device that enables operation of device 1100 as described herein, such as, but not limited to, alignment tabs, alignment pins, alignment slots and/or grooves, and alignment lines inscribed on probe segment 308 and portions of device 1100.

In operation, to rotate probe segment 308, drive device 1122 induces a clockwise rotational movement to driving gear 1118. Driving gear 1118 then induces a counter-clockwise rotational movement to driven gear 1120. Driven gear 1120 subsequently induces a clockwise rotational movement to probe segment 308 via gear ring 1110. Also, in operation, for opposite rotation of probe segment 308, drive device 1122 induces a counter-clockwise rotational movement to driving gear 1118. Driving gear 1118 then induces a clockwise rotational movement to driven gear 1120. Driven gear 1120 subsequently induces a counter-clockwise movement to probe segment 308 via gear ring 1110.

Figure 23:
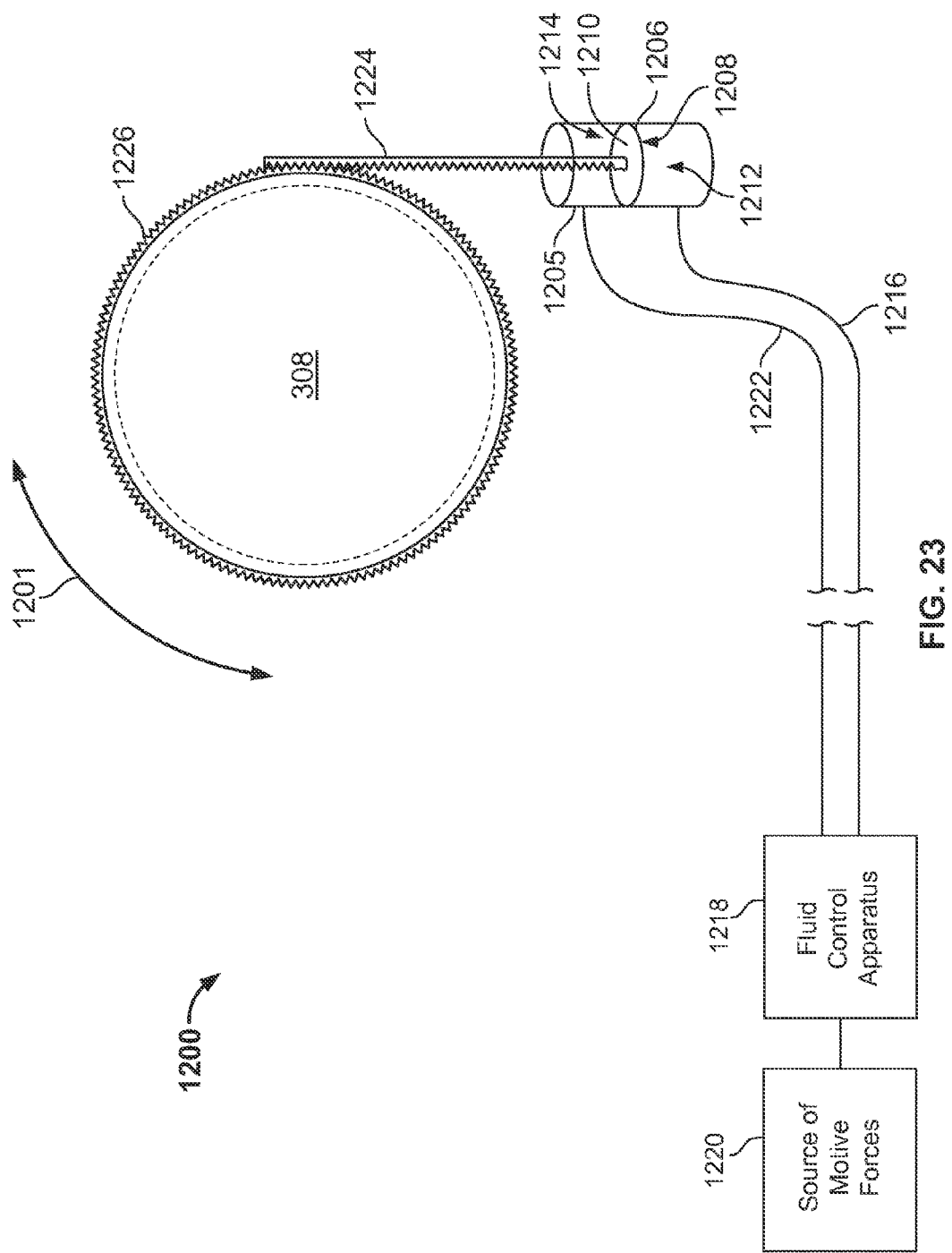
FIG. 23 is a schematic axial view of another alternative rotational positioning device that may be used with the sampling probe transport devices shown in FIGS. 14, 15, 17, 18, and 19.

FIG. 23 is a schematic axial view of another alternative rotational positioning device 1200 that may be used with sampling probe transport devices 700, 800, 900, and 1000 (shown in FIGS. 14 and 15, 16, 17, 18, and 19, respectively). Device 1200 facilitates automatic control of rotation of probe segment 308 within exhaust stack 200 (shown in FIGS. 14 through 19) as indicated by arrow 1201. More specifically, device 1200 facilitates automation of sampling and velocity traverse of exhaust fluid stream 124 (shown in FIGS. 1 through 4 and 11 through 13) in exhaust stack 200.

In this embodiment, device 1200 is a fluid-drive device that includes a sealed enclosure 1205, or casing 1205. Enclosure 1205 is substantially cylindrical and facilitates operation of device 1200 with a pressurized fluid. Alternatively, enclosure 1205 has any shape that enables operation of device 1200 as described herein. In the exemplary embodiment, device 1200 includes a positioning device 1206, such as, a ram. Moreover, device 1206 is slidably coupled with enclosure 1205, and includes a first motive surface 1208 and a second motive surface 1210. Alternatively, any positioning device that enables operation of device 1200 as described herein, may be used.

In the exemplary embodiment, first motive surface 1208 and enclosure 1205 at least partially define a first pressure rotation cavity 1212. Similarly, second motive surface 1210 and enclosure 1205 at least partially define a second pressure rotation cavity 1214. Also, in this embodiment, device 1200 includes a first fluid conduit 1216 that is coupled in flow communication with cavity 1212 and with a fluid control apparatus 1218. Fluid control apparatus 1218 is coupled in flow communication with a fluid source 1220.

Further, in this embodiment, device 1200 includes a second fluid conduit 1222 that is coupled in flow communication with cavity 1214 and fluid control apparatus 1218. Moreover, in the exemplary embodiment, the motive fluid used is pressurized air. Alternatively, any fluid that enables operation of device 1200 as described herein may be used. Also, in this alternative embodiment, device 1200 includes a toothed positioning arm 1224 that is engaged to an arcual toothed device 1226, such as, a toothed positioning ring 1226. Device 1226 is rotatably coupled to probe segment 308, and arm 1224 is securely coupled to ram 1206.

In operation, to rotate probe segment 308 counter-clockwise, pressurized air is channeled to insertion cavity 1212 from source 1220 via control apparatus 1218 and conduit 1216. Because air pressure within cavity 1212 is greater than air pressure in cavity 1214, a motive force is induced on surface 1208. Ram 1210 is moved such that it drives arm 1224 to rotate ring 1226, and probe segment 308, in a counter-clockwise direction. Also, in operation, to rotate probe segment 308 clockwise, pressurized air is channeled to insertion cavity 1214 from source 1220 via control apparatus 1218 and conduit 1222. Because air pressure within cavity 1214 is greater than air pressure in cavity 1212, a linear motive force is induced on surface 1210. Ram 1210 is transported such that it drives arm 1224 to rotate ring 1226, and probe segment 308, in a clockwise direction.

Figure 24:
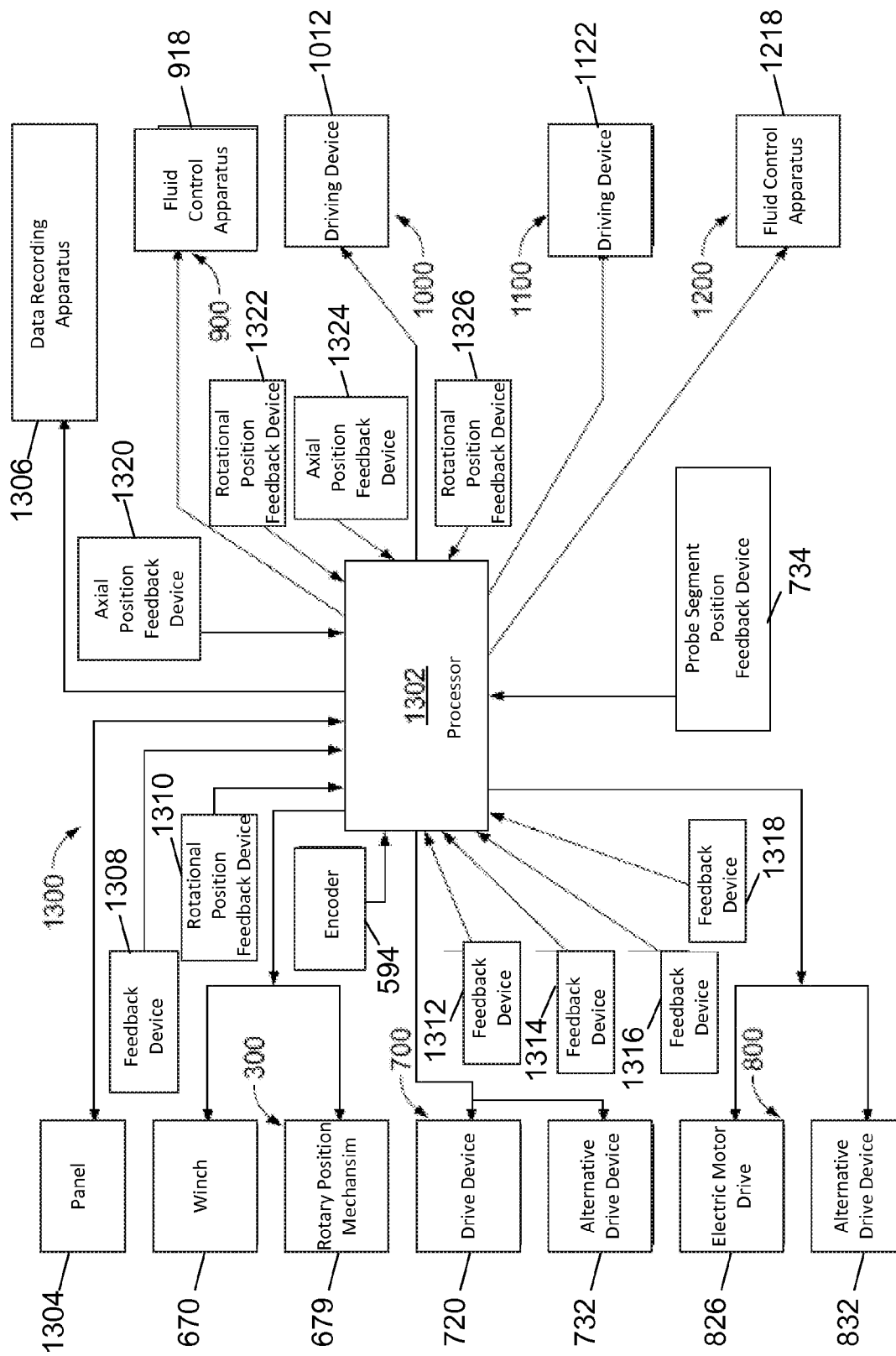
FIG. 24 is a schematic view of a probe position control system that may be used with the sampling probe transport devices shown in FIGS. 3, 4, 5, 13, 14, 15, 17, 18, and 19.

FIG. 24 is a schematic view of a probe position control system 1300 that may be used with sampling probe transport devices 300, 700, 800, 900, and 1000. A technical effect of control system 1300 is that control system 1300 facilitates remote, automatic, accurate, and precise axial and rotational positioning of probe segment 308 (shown in FIGS. 3, 4, 11 through 15, and 17 through 22) within exhaust stack 200 (shown in FIGS. 2, 3, 4, and 14 through 19). Moreover, system 1300 facilitates sampling and velocity traverse of exhaust fluid stream 124 (shown in FIGS. 1 through 4 and 11 through 13) in exhaust stack 200. In all of the embodiments described herein, control system 1300 is constructed, configured, and implemented for at least one of devices 300, 700, 800, 900, and 1000 and for any combination thereof.

In all of the embodiments described herein, control system 1300 includes at least one processor 1302. Processor 1302 is any processing device that enables operation of control system 1300 as described herein including, but not limited to, programmable logic controllers (PLCs), distributed control systems (DCS'), and personal computers. Processor 1302 is programmed with a plurality of fluid sampling schemes (not shown). Each fluid sampling scheme includes predetermined axial extension sampling length profiles and rotational position sampling profiles. Also, each sampling scheme is programmed with a predetermined periodicity. Each fluid sampling scheme is either automatically or manually initiated.

Control system 1300 also includes at least one operator control and monitoring panel 1304. Panel 1304 facilitates remote monitoring of sampling activities. Control system 1300 also includes a data recording apparatus 1306. Data recording apparatus 1306 is any data storage device that enables operation of control system 1300 as described herein including, but not limited to, solid state recorders, compact disc recorders, and tape devices. Control system 1300 provides the technical effect of control of axial and rotational positioning of any embodiment of sampling probe transport device described herein.

In the embodiments associated with sampling probe transport device 300, processor 1302 is coupled with push chain winch 670 and rotary position mechanism 679. Processor 1302 is programmed with a predetermined length of extension of device 300 and rotational positioning of probe 308 for each fluid sampling scheme programmed therein. Processor 1302 transmits positioning command signals to winch 670 and to mechanism 679. Control system 1300 also includes an axial position feedback device 1308 and a rotational position feedback device 1310. A first technical effect is that processor 1302 communicates with feedback devices 1308 and 1310, to control an insertion depth $D_I$ (shown in FIG. 13) of probe segment 308 within exhaust stack 200. A second technical effect is that processor 1302 also communicates with rotary position encoder 594 to control a rotational position of sample tube 584 (shown in FIGS. 11 and 13) with respect to exhaust fluid stream 124 (shown in FIGS. 1 through 4 and 11 through 13).

Feedback device 1308 is any device that enables operation of control system 1300 and device 300 as described herein including, but not limited to, an encoder device and a linear position transducer. Encoder devices include, but are not limited to, a chain link encoder that counts links in push chain 672 (shown in FIG. 13) and a motor rotor position encoder and/or transducer embedded within winch 670. Feedback device 1310 is any device that enables operation of control system 1300 and device 300 as described herein including, but not limited to, a rotational encoder device and a rotational position transducer.

In the embodiments associated with sampling probe transport device 700, processor 1302 is coupled with pneumatic drive device 720 and/or alternative drive device 732. Processor 1302 is programmed with a predetermined length of extension of device 700 and rotational positioning of probe 308 for each fluid sampling scheme programmed therein. Processor 1302 transmits positioning command signals to each of drive device 720 and/or drive device 732.

In addition, processor 1302 is also coupled to probe segment position feedback device 734 that facilitates the technical effect of measuring a length of probe segment 308 as it extends through support block 730 (shown in FIGS. 14, 15, and 16), thereby facilitating a technical effect of control of a position of carriage 712 (shown in FIGS. 14 and 15) and therefore, insertion depth $D_I$ (shown in FIG. 15) of probe segment 308 within exhaust stack 200. Device 734 is one of a friction-driven wheel sensor, an encoding sensor, and a linear position transducer. Alternatively, device 734 is any apparatus that enables operation of device 700 as described herein. Also, device 734 measures rotational positions of probe segment 308, thereby facilitating a technical effect of rotary position control of probe segment 308. As such, device 734 is at least one of, and not limited to, a rotational position encoder and a rotational position transducer.

Alternatively, in the embodiments associated with sampling probe transport device 700 and rather than, or in addition to device 734, control system 1300 also includes an axial position feedback device 1312 and a rotational position feedback device 1314. Processor 1302 is in communication with feedback devices 1312 and 1314. Feedback device 1312 is any device that enables operation of control system 1300 and device 700 as described herein including, but not limited to, a linear position transducer embedded within slide track 708 (shown in FIGS. 14 and 15). Additional examples of device 1312, that is, encoder devices embedded within device 732 include, but are not limited to, a chain link encoder, a cable length encoder, a gear tooth encoder, and a motor rotor position encoder and/or transducer.

Also, alternatively, feedback device 1314 is any device that enables operation of control system 1300 and device 300 as described herein, including, but not limited to, a rotational encoder device and a rotational position transducer proximate to probe segment 308. Moreover, alternatively, device 1314 is embedded within rotational positioning devices 1100 and/or 1200 and includes, but is not limited to, a gear tooth encoder, a motor rotor position encoder and/or transducer, and a ram position encoder and/or transducer.

In the embodiments associated with sampling probe transport device 800, processor 1302 is coupled with electric motor drive 826 and/or alternative drive device 832. Processor 1302 is programmed with a predetermined length of extension of device 800 and rotational positioning of probe 308 for each fluid sampling scheme programmed therein. Processor 1302 transmits positioning command signals to each of electric motor drive 826 and/or alternative drive device 832.

In addition, processor 1302 is also coupled to probe segment position feedback device 734 that facilitates a technical effect of measuring a length of probe segment 308 as it extends through support block 730, thereby facilitating a technical effect of control of a position of motorized car 818 (shown in FIG. 17) and therefore, insertion depth $D_I$ of probe segment 308 within exhaust stack 200. Device 734 is one of a friction-driven wheel sensor, an encoding sensor, and a linear position transducer. Alternatively, device 734 is any apparatus that enables operation of device 800 as described herein. Also, device 734 measures rotational positions of probe segment 308, thereby facilitating a technical effect of rotary position control of probe segment 308. As such, device 734 is at least one of, and not limited to, a rotational position encoder and a rotational position transducer.

Alternatively, in the embodiments associated with sampling probe transport device 800 and rather than, or in addition to device 734, control system 1300 also includes an axial position feedback device 1316 and a rotational position feedback device 1318. Processor 1302 is in communication with feedback devices 1316 and 1318. Feedback device 1316 is any device that enables operation of control system 1300 and device 800 as described herein including, but not limited to, a linear position transducer embedded within floor 824 (shown in FIG. 17), roller and/or wheel rotational encoders and/or transducers embedded within second portion of carriage 816 (shown in FIG. 17), and a motor rotor position encoder and/or transducer embedded within electric motor drive 826 (shown in FIG. 17). Additional examples of device 1316, that is, encoder devices embedded within device 832 include, but are not limited to, a chain link encoder, a cable length encoder, and a gear tooth encoder.

Also, alternatively, feedback device 1318 is any device that enables operation of control system 1300 and device 800 as described herein, including, but not limited to, a rotational encoder device and a rotational position transducer proximate to probe segment 308. Moreover, alternatively, device 1318 is embedded within rotational positioning devices 1100 and/or 1200 and includes, but is not limited to, a gear tooth encoder, a motor rotor position encoder and/or transducer, and a ram position encoder and/or transducer.

In the embodiments associated with sampling probe transport device 900, processor 1302 is coupled with fluid control apparatus 918. Processor 1302 is programmed with a predetermined length of extension of device 900 and rotational positioning of probe 308 for each fluid sampling scheme programmed therein. Processor 1302 transmits positioning command signals to fluid control apparatus 918.

In addition, processor 1302 is also coupled to probe segment position feedback device 734 that facilitates a technical effect of measuring a length of probe segment 308 as it extends through support block 730, thereby facilitating a technical effect of control of a position of diaphragm 906 (shown in FIG. 18) and therefore, insertion depth $D_I$ of probe segment 308 within exhaust stack 200. Device 734 is one of a friction-driven wheel sensor, an encoding sensor, and a linear position transducer. Alternatively, device 734 is any apparatus that enables operation of device 900 as described herein. Also, device 734 measures rotational positions of probe segment 308, thereby facilitating a technical effect of rotary position control of probe segment 308. As such, device 734 is at least one of, and not limited to, a rotational position encoder and a rotational position transducer.

Alternatively, in the embodiments associated with sampling probe transport device 900 and rather than, or in addition to device 734, control system 1300 also includes an axial position feedback device 1320 and a rotational position feedback device 1322. Processor 1302 is in communication with feedback devices 1320 and 1322. Feedback device 1322 is any device that enables operation of control system 1300 and device 900 as described herein including, but not limited to, linear position encoders and/or transducers embedded within sealed enclosure 905 (shown in FIG. 18).

Also, alternatively, feedback device 1322 is any device that enables operation of control system 1300 and device 900 as described herein, including, but not limited to, a rotational encoder device and a rotational position transducer proximate to probe segment 308. Moreover, alternatively, device 1322 is embedded within rotational positioning devices 1100 and/or 1200 and includes, but is not limited to, a gear tooth encoder, a motor rotor position encoder and/or transducer, and a ram position encoder and/or transducer.

In the embodiments associated with sampling probe transport device 1000, processor 1302 is coupled with driving device 1012. Processor 1302 is programmed with a predetermined length of extension of device 1000 and rotational positioning of probe 308 for each fluid sampling scheme programmed therein. Processor 1302 transmits positioning command signals to driving device 1012.

In addition, processor 1302 is also coupled to probe segment position feedback device 734 that facilitates a technical effect of measuring a length of probe segment 308 as it extends through support block 730, thereby facilitating a technical effect of control of insertion depth $D_I$ of probe segment 308 within exhaust stack 200. Device 734 is one of a friction-driven wheel sensor, an encoding sensor, and a linear position transducer. Alternatively, device 734 is any apparatus that enables operation of device 1000 as described herein. Also, device 734 measures rotational positions of probe segment 308, thereby facilitating a technical effect of rotary position control of probe segment 308. As such, device 734 is at least one of, and not limited to, a rotational position encoder and a rotational position transducer.

Alternatively, in the embodiments associated with sampling probe transport device 1000 and rather than, or in addition to device 734, control system 1300 also includes an axial position feedback device 1324 and a rotational position feedback device 1326. Processor 1302 is in communication with feedback devices 1324 and 1326. Feedback device 1324 is any device that enables operation of control system 1300 and device 1000 as described herein including, but not limited to, linear position encoders and/or transducers proximate to probe segment 308.

Also, alternatively, feedback device 1326 is any device that enables operation of control system 1300 and device 1000 as described herein, including, but not limited to, a rotational encoder device and a rotational position transducer proximate to probe segment 308. Moreover, alternatively, device 1326 is embedded within rotational positioning devices 1100 and/or 1200 and includes, but is not limited to, a gear tooth encoder, a motor rotor position encoder and/or transducer, and a ram position encoder and/or transducer.

Described herein are exemplary embodiments of apparatus that facilitate measuring emissions within exhaust stacks. Specifically, the apparatus as described herein, and more specifically, a telescoping monitoring probe device, facilitates reducing a physical footprint of probe devices in the vicinity of an exhaust stack or duct. Reducing such a physical footprint facilitates increasing personal access and increasing available space for other equipment in the vicinity of the exhaust stack or duct. Moreover, reducing a size of the probe device reduces material and manufacturing costs and shipping costs. Also, specifically, automation of emissions sampling and testing reduces a potential for operator error and reduces a period of time for conducting testing and sampling activities, typically performed at low production levels. Subsequently, time spent at low production levels is reduced and costs of sampling and testing are reduced due to the reduced time for performance as well as a reduced number of resources to control testing and sampling.

The methods and systems described herein are not limited to the specific embodiments described herein. For example, components of each system and/or steps of each method may be used and/or practiced independently and separately from other components and/or steps described herein. In addition, each component and/or step may also be used and/or practiced with other assembly packages and methods.

While the invention has been described in terms of various specific embodiments, those skilled in the art will recognize that the invention can be practiced with modification within the spirit and scope of the claims.

What is claimed is:

1. A transport device comprising:
   a first segment fixedly coupled to a wall;
   at least one second segment coupled to said first segment, said at least one second segment comprises at least one of a fluid-driven device, a rack and pinion drive device, and a carriage, said at least one second segment further comprising at least one extension and retraction assembly comprising an outer telescoping tube and an inner telescoping tube, each of said outer telescoping tube and said inner telescoping tube having a substantially diamond shaped cross-sectional shape;
   a probe segment coupled to said at least one extension and retraction assembly; and an automated position control system comprising:
- at least one axial positioning device coupled to said at least one second segment; and
- at least one axial position feedback device coupled to at least one of said first segment and said at least one second segment.

2. A transport device in accordance with claim 1, wherein said at least one extension and refraction assembly comprises:
- at least one slidable surface; and
- a carriage slidably coupled to said at least one slidable surface.

3. A transport device in accordance with claim 2 further comprising at least one of an electrical drive device, a pneumatic drive device, a cable drive device, and a chain drive device drivingly coupled to said carriage.

4. A transport device in accordance with claim 1, wherein said first segment comprises a support block, said probe segment is slidingly coupled to said support block.

5. A transport device in accordance with claim 1, wherein said fluid-driven device comprises:
- a casing;
- a positioning device coupled to said probe segment, at least a portion of said positioning device is slidably coupled within said casing, said positioning device comprising a first motive surface and a second motive surface; and
- at least one motive fluid conduit coupled in flow communication with at least one of said first motive and said second motive surfaces.

6. A transport device in accordance with claim 1, wherein said positioning device is one of a ram, a piston, and a diaphragm.

7. A transport device in accordance with claim 1, wherein said automated position control system further comprises at least one probe rotary positioning mechanism comprising at least one of:
- at least one rotary positioning device; and
- at least one rotary position feedback device.

8. A transport device in accordance with claim 7, wherein said at least one rotary position feedback device comprises at least one of:
- a rotational position encoder;
- a rotational position transducer;
- a gear tooth encoder;
- a motor rotor position encoder;
- a motor rotor position transducer;
- a fluid positioning device position encoder; and
- a fluid positioning device position transducer.

9. A transport device in accordance with claim 1, wherein said carriage comprises a motorized car.

10. A transport device in accordance with claim 1, wherein said rack and pinion drive device comprises:
- at least one of an electrically-driven motor and a fluid-driven motor; and
- at least one driving gear rotatably coupled to one of said at least one of an electrically-driven motor and a fluid-driven motor.

11. A transport device in accordance with claim 1, wherein said at least one axial position feedback device comprises at least one of:
- a friction-driven wheel sensor;
- a linear position encoder;
- a linear position transducer;
- a gear tooth encoder;
- a motor rotor position encoder;
- a motor rotor position transducer;
- a fluid positioning device position encoder; and
- a fluid positioning device position transducer.

* * * * *